US009980509B2

(12) United States Patent
Marshall et al.

(10) Patent No.: US 9,980,509 B2
(45) Date of Patent: *May 29, 2018

(54) MODIFICATION OF BACTERIAL PROFILE OF TOBACCO

(71) Applicant: R.J. REYNOLDS TOBACCO COMPANY, Winston-Salem, NC (US)

(72) Inventors: Jerry Wayne Marshall, Stokesdale, NC (US); Anthony Richard Gerardi, Winston-Salem, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 295 days.

This patent is subject to a terminal disclaimer.

(21) Appl. No.: 15/043,177

(22) Filed: Feb. 12, 2016

(65) Prior Publication Data

US 2016/0157516 A1 Jun. 9, 2016

Related U.S. Application Data

(63) Continuation-in-part of application No. 14/870,526, filed on Sep. 30, 2015, now Pat. No. 9,681,681, which
(Continued)

(51) Int. Cl.
A24B 15/18 (2006.01)
A01D 45/16 (2006.01)
(Continued)

(52) U.S. Cl.
CPC ............ *A24B 15/183* (2013.01); *A01D 45/16* (2013.01); *A01N 59/08* (2013.01); *A24B 1/00* (2013.01);
(Continued)

(58) Field of Classification Search
CPC ......... A24B 15/18; A24B 15/183; A24B 1/00; A24B 3/12; A24B 13/00; A24B 15/20;
(Continued)

(56) References Cited

U.S. PATENT DOCUMENTS 1,327,692 A 1/1920 Beinhart
2,758,603 A 8/1956 Heljo
(Continued)

FOREIGN PATENT DOCUMENTS

WO WO 83/01180 4/1983
WO WO 98/05226 2/1998
(Continued)

OTHER PUBLICATIONS

Andersen et al., "Effect of Storage Conditions on Nitrosated, Acylated, and Oxidized Pyridine Alkaloid Derivatives in Smokeless Tobacco Products," *Cancer Research*, vol. 49, 1989, pp. 5895-5900.
(Continued)

*Primary Examiner* — Dennis R Cordray
(74) *Attorney, Agent, or Firm* — Womble Bond Dickinson (US) LLP

(57) ABSTRACT

A method of modifying the content of certain bacteria in uncured tobacco material is provided, the method including contacting an uncured tobacco material with a treatment solution, wherein the treatment solution is selected from the group consisting of: (i) a solution comprising salt, sugar, or a combination thereof; (ii) a solution comprising one or more enzymes; and (iii) a solution comprising one or more probiotics, wherein said contacting provides a treated tobacco material having a reduced total bacterial content following harvest. Also provided is a method of reducing TSNA content, the method including growing a tobacco plant in soil treated with a chloride source; harvesting the tobacco plant; and curing the harvested tobacco plant to give a cured tobacco material, providing a treated, cured tobacco material having a TSNA content that is reduced as compared to a cured tobacco material that has been grown in soil not treated with a chloride source. Smoking articles and smokeless tobacco products including such treated tobacco materials are also provided.

25 Claims, 2 Drawing Sheets

Related U.S. Application Data is a continuation of application No. 13/857,677, filed on Apr. 5, 2013, now Pat. No. 9,155,334.

(51) Int. Cl.

| | | |
|---|---|---|
| *A24B 3/12* | (2006.01) | |
| *A24B 13/00* | (2006.01) | |
| *A01N 59/08* | (2006.01) | |
| *A24B 1/00* | (2006.01) | |
| *A24B 15/20* | (2006.01) | |
| *A24B 15/30* | (2006.01) | |
| *A24B 15/24* | (2006.01) | |

(52) U.S. Cl.
CPC .............. *A24B 3/12* (2013.01); *A24B 13/00* (2013.01); *A24B 15/20* (2013.01); *A24B 15/245* (2013.01); *A24B 15/307* (2013.01)

(58) Field of Classification Search
CPC ..... A24B 15/28; A24B 15/287; A24B 15/245; A24B 15/307; A01D 45/16; A01N 59/06–59/08
USPC ...... 131/290, 300, 309, 347, 352; 47/58.1 R, 47/58.1 SC, 58.1 SE, 58.1 FV
See application file for complete search history.

(56) References Cited

U.S. PATENT DOCUMENTS

| | | | |
|---|---|---|---|
| 3,132,651 A | 5/1964 | Kiefer | |
| 3,240,214 A | 3/1966 | Bavley et al. | |
| 3,513,857 A | 5/1970 | Silberman | |
| 3,612,065 A | 10/1971 | Rosen | |
| 3,636,097 A | 1/1972 | Harvey | |
| 3,943,945 A | 3/1976 | Rosen | |
| 4,061,488 A | 12/1977 | Mann | |
| 4,135,521 A | 1/1979 | Malan et al. | |
| 4,140,136 A | 2/1979 | Geiss et al. | |
| 4,151,848 A | 5/1979 | Newton et al. | |
| 4,307,733 A | 12/1981 | Teng et al. | |
| 4,308,877 A | 1/1982 | Mattina | |
| 4,343,317 A | 8/1982 | Bokelman | |
| 4,343,318 A | 8/1982 | Brenik et al. | |
| 4,347,859 A | 9/1982 | Bokelman et al. | |
| 4,407,307 A | 10/1983 | Gaisch et al. | |
| 4,476,881 A | 10/1984 | Gravely et al. | |
| 4,528,993 A | 7/1985 | Sensabaugh, Jr. et al. | |
| 4,556,073 A | 12/1985 | Gravely et al. | |
| 4,557,280 A | 12/1985 | Gravely et al. | |
| 4,566,469 A | 1/1986 | Semp et al. | |
| 4,572,219 A | 2/1986 | Gaisch et al. | |
| 4,660,577 A | 4/1987 | Sensabaugh et al. | |
| 4,709,710 A | 12/1987 | Gaisch et al. | |
| 4,716,911 A | 1/1988 | Poulose et al. | |
| 4,819,668 A | 4/1989 | Shelar et al. | |
| 4,887,618 A | 12/1989 | Bernasek et al. | |
| 4,941,484 A | 7/1990 | Clapp et al. | |
| 5,099,862 A | 3/1992 | White et al. | |
| 5,343,879 A | 9/1994 | Teague | |
| 5,372,149 A | 12/1994 | Roth et al. | |
| 5,387,416 A | 2/1995 | White et al. | |
| 5,601,097 A | 2/1997 | De Grandpré et al. | |
| 5,676,164 A | 10/1997 | Martin | |
| 5,803,081 A | 9/1998 | O'Donnell, Jr. et al. | |
| 5,869,042 A | 2/1999 | Marrone et al. | |
| 6,202,649 B1 | 3/2001 | Williams | |
| 6,564,808 B1 | 5/2003 | Hempfling et al. | |
| 6,755,200 B1 | 6/2004 | Hempfling et al. | |
| 6,805,134 B2 | 10/2004 | Peele | |
| 6,834,654 B2 | 12/2004 | Williams | |
| 6,895,974 B2 | 5/2005 | Peele | |
| 7,025,066 B2 | 4/2006 | Lawson et al. | |
| 7,293,564 B2 | 11/2007 | Perfetti et al. | |
| 7,549,425 B2 | 6/2009 | Koga et al. | |
| 7,549,426 B2 | 6/2009 | Koga et al. | |
| 7,556,046 B2 | 7/2009 | Koga et al. | |
| 8,353,300 B2 | 1/2013 | Li et al. | |
| 8,905,041 B2 | 12/2014 | Li et al. | |
| 9,271,524 B1 | 3/2016 | Chipley | |
| 9,681,681 B2 * | 6/2017 | Moldoveanu | A24B 15/20 |
| 2003/0056801 A1 | 3/2003 | Krauss et al. | |
| 2005/0072047 A1 | 4/2005 | Conkling et al. | |
| 2006/0037623 A1 | 2/2006 | Lawrence, Jr. | |
| 2006/0196516 A1 | 9/2006 | Cui et al. | |
| 2006/0225750 A1 | 10/2006 | Koga et al. | |
| 2008/0152684 A1 | 6/2008 | Tzeng et al. | |
| 2008/0202538 A1 * | 8/2008 | Li | A01G 7/06 131/309 |
| 2008/0245377 A1 | 10/2008 | Marshall et al. | |
| 2010/0116281 A1 | 5/2010 | Marshall et al. | |
| 2012/0125354 A1 | 5/2012 | Byrd et al. | |
| 2012/0234334 A1 | 9/2012 | Chen et al. | |
| 2012/0279510 A1 | 11/2012 | Marshall et al. | |
| 2013/0269719 A1 | 10/2013 | Marshall et al. | |
| 2014/0020694 A1 | 1/2014 | Moldoveanu et al. | |
| 2015/0315603 A1 | 11/2015 | Bovet et al. | |

FOREIGN PATENT DOCUMENTS

| | | |
|---|---|---|
| WO | WO 98/58555 | 12/1998 |
| WO | WO 00/02464 | 1/2000 |
| WO | WO 02/13636 | 2/2002 |
| WO | WO 03/094639 | 11/2003 |

OTHER PUBLICATIONS

Ellis et al., "Bacterial Diseases of Plants," *The Ohio State University, Fact Sheet, Agriculture and Natural Resources*, 2008. http://ohioline.osu.edu/hyg-fact/3000/.

Heyser et al., "Osmotic Adjustment of Cultured Tobacco Cells (*Nicotiana tabacum* var. *Samsum*) Grown on Sodium Chloride," *Plant Physiol.*, 1981, pp. 720-727, vol. 67.

Huang et al., "Bacterial Diversities on Unaged and Aging Flu-Cured Tobacco Leaves Estimated by 16S rRNA Sequence Analysis," *Appl. Microbiol. Biotechnol.*, 2010, pp. 553-562, vol. 88, No. 2.

Larsson et al., "Identification of Bacterial and Fungal Components in Tobacco and Tobacco Smoke," *Tobacco Induced Diseases*, 2008, pp. 1-8, vol. 4, No. 4. http://www.tobaccoinduceddiseases.com/content/4/1/4.

Larsson et al., "Microbiological Components in Mainstream and Sidestream Cigarette Smoke," *Tobacco Induced Diseases*, 2012, pp. 1-5, vol. 10, No. 13. http://www.tobaccoinduceddiseases.com/content/10/1/13.

Mitchell, "Changes in the Microflora of Tobacco Leaves During Field Growth in England," *Paper for Presentation: Coresta Meeting*, Cesme, Turkey, Oct. 1989, http://legacy.library.ucsf.edu/tid/num81a99/pdf.

Müller et al. "Isolation and Characterization of Cell Lines of *Nicotiana* Tabacum Nitrate Reductase," *Molec. Gen. Genet.* 161, pp. 67-76 (1978).

Tyx et al. "Characterization of Bacterial Communities in Selected Smokeless Tobacco Products Using 16S rDNA Analysis," *PLOS One*, DOI: 10.1371/journal.pone.0146939, Jan. 19, 2016, pp. 1-21.

West et al., "Irrigation Timing—Its influence on the Effects of Salinity and Waterlogging Stresses in Tobacco Plants," *Soil Science*, 1978, vol. 125, No. 6, pp. 367-376.

Yu Qing-fu, Modern Sanitary Microbiology, p. 168-173, People's Medical Publishing House, edition 1, Sep. 30, 1995.

Zhang Qing, et al., Microbiology, p. 142-143, Science Press, edition 1, Aug. 31, 2004.

\* cited by examiner

MODIFICATION OF BACTERIAL PROFILE OF TOBACCO

CROSS-REFERENCE TO RELATED APPLICATIONS

The present application is a continuation-in-part of U.S. patent application Ser. No. 14/870,526, filed Sep. 30, 2015, which is a continuation of U.S. patent application Ser. No. 13/857,677, filed Apr. 5, 2013. Both applications are incorporated herein by reference in their entireties.

FIELD OF THE INVENTION

The present invention relates to plants and modifications to the method of growing, harvesting, and/or treating plants (e.g., tobacco). Particularly, the present invention relates to products made or derived from tobacco, or that otherwise incorporate tobacco, and are intended for human consumption.

BACKGROUND OF THE INVENTION

Popular smoking articles, such as cigarettes, have a substantially cylindrical rod shaped structure and include a charge, roll or column of smokable material such as shredded tobacco (e.g., in cut filler form) surrounded by a paper wrapper thereby forming a so-called "tobacco rod." Normally, a cigarette has a cylindrical filter element aligned in an end-to-end relationship with the tobacco rod. Typically, a filter element comprises plasticized cellulose acetate tow circumscribed by a paper material known as "plug wrap." Certain cigarettes incorporate a filter element having multiple segments, and one of those segments can comprise activated charcoal particles. Typically, the filter element is attached to one end of the tobacco rod using a circumscribing wrapping material known as "tipping paper." It also has become desirable to perforate the tipping material and plug wrap, in order to provide dilution of drawn mainstream smoke with ambient air. A cigarette is employed by a smoker by lighting one end thereof and burning the tobacco rod. The smoker then receives mainstream smoke into his/her mouth by drawing on the opposite end (e.g., the filter end) of the cigarette.

The tobacco used for cigarette manufacture is typically used in blended form. For example, certain popular tobacco blends, commonly referred to as "American blends," comprise mixtures of flue-cured tobacco, burley tobacco and Oriental tobacco, and in many cases, certain processed tobaccos, such as reconstituted tobacco and processed tobacco stems. The precise amount of each type of tobacco within a tobacco blend used for the manufacture of a particular cigarette brand varies from brand to brand. However, for many tobacco blends, flue-cured tobacco makes up a relatively large proportion of the blend, while Oriental tobacco makes up a relatively small proportion of the blend. See, for example, *Tobacco Encyclopedia*; Voges, E. (Ed.), 1984; pp 44-45, Browne, C. *The Design of Cigarettes,* 3rd ed.; 1990; p 43; and *Tobacco: Production, Chemistry and Technology*; Davis, D. and Nielsen, M. (Eds.); 1999; p 346.

Tobacco also may be enjoyed in a so-called "smokeless" form. Particularly popular smokeless tobacco products are employed by inserting some form of processed tobacco or tobacco-containing formulation into the mouth of the user. Various types of smokeless tobacco products are known. See for example, the types of smokeless tobacco formulations, ingredients, and processing methodologies set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0196730 to Engstrom et al.; 2008/0209586 to Neilsen et al.; 2008/0305216 to Crawford et al.; 2009/0065013 to Essen et al.; 2009/0293889 to Kumar et al.; 2010/0291245 to Gao et al; and 2011/0139164 to Mua et al.; PCT WO 04/095959 to Arnarp et al. and WO 2010/132444 to Atchley; each of which is incorporated herein by reference.

One type of smokeless tobacco product is referred to as "snuff." Representative types of moist snuff products, commonly referred to as "snus," have been manufactured in Europe, particularly in Sweden, by or through companies such as Swedish Match AB, Fiedler & Lundgren AB, Gustavus AB, Skandinavisk Tobakskompagni A/S, and Rocker Production AB. Snus products available in the U.S.A. have been marketed under the tradenames Camel Snus Frost, Camel Snus Original and Camel Snus Spice by R. J. Reynolds Tobacco Company. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard. Representative smokeless tobacco products also have been marketed under the tradenames Oliver Twist by House of Oliver Twist A/S; Copenhagen, Skoal, SkoalDry, Rooster, Red Seal, Husky, and Revel by U.S. Smokeless Tobacco Co.; "taboka" by Philip Morris USA; Levi Garrett, Peachy, Taylor's Pride, Kodiak, Hawken Wintergreen, Grizzly, Dental, Kentucky King, and Mammoth Cave by Conwood Company, LLC; and Camel Orbs, Camel Sticks, and Camel Strips by R. J. Reynolds Tobacco Company.

Through the years, various treatment methods and additives have been proposed for altering the overall character or nature of tobacco materials utilized in tobacco products. For example, additives or treatment processes have been utilized in order to alter the chemistry or sensory properties of the tobacco material, or in the case of smokable tobacco materials, to alter the chemistry or sensory properties of mainstream smoke generated by smoking articles including the tobacco material. Various types of enzymes, bacteria, and microorganisms (e.g., fungi and yeast) have been employed in conjunction with tobacco for the purpose of altering the chemical makeup of the tobacco, e.g., by reducing the content of certain chemical compounds. See, for example, U.S. Pat. No. 3,132,651 to Keifer; U.S. Pat. No. 3,513,857 to Silberman; U.S. Pat. No. 3,240,214 to Bavley; U.S. Pat. No. 3,636,097 to Harvey; U.S. Pat. No. 3,612,065 to Rosen; U.S. Pat. No. 3,943,945 to Rosen; U.S. Pat. No. 4,135,521 to Malan; U.S. Pat. No. 4,140,136 to Geiss et al.; U.S. Pat. No. 4,151,848 to Newton et al.; U.S. Pat. No. 4,307,733 to Teng; U.S. Pat. No. 4,308,877 to Mattina et al.; U.S. Pat. No. 4,407,307 to Gaisch; U.S. Pat. No. 4,476,881 to Gravely et al.; U.S. Pat. No. 4,556,073 to Gravely et al.; U.S. Pat. No.

4,557,280 to Gravely et al.; U.S. Pat. No. 4,566,469 to Semp et al.; U.S. Pat. No. 4,572,219 to Gaisch; U.S. Pat. No. 4,709,710 to Gaisch; U.S. Pat. No. 4,716,911 to Poulose; U.S. Pat. No. 4,887,618 to Bernasek; U.S. Pat. No. 4,941,484 to Clapp; U.S. Pat. No. 5,099,862 to White; U.S. Pat. No. 5,343,879 to Teague; U.S. Pat. No. 5,372,149 to Roth et al.; U.S. Pat. No. 5,601,097 to DeGranpreet; U.S. Pat. No. 7,549,425 to Koga et al.; U.S. Pat. No. 7,549,426 to Koga et al.; and U.S. Pat. No. 7,556,046 to Koga et al.; Int. Appl. Publ. No. WO 2000/02464 to Kierulff; and EP Appl. No. 1094724 to Kierulff, which are all incorporated herein by reference.

Nitrosamines are known to be present in air, foods, beverages, cosmetics, and even pharmaceuticals. Preussman, R. et al., In *Chemical Carcinogens*, 2nd ed., Vol. 2, Searle, C. E. (Ed.); ACS Monograph 182; 1984; pp 829-868. Tobacco and tobacco smoke also are known to contain nitrosamines. Green et al. *Rec. Adv. Tob. Sci.* 1996, 22, 131. Tobacco is known to contain a class of nitrosamines known as tobacco specific nitrosamines (TSNAs). Hecht, S. *Chem. Res. Toxicol.* 1998, 11, 6, 559-603; Hecht, S. *Mut. Res.* 1999, 424, 1-2, 127-142. TSNAs have been reported to be present in smokeless tobacco, Brunnemann, K. et al. *Canc. Lett.* 1987, 37, 7-16, Tricker, A. *Canc. Lett.* 1988, 42, 113-118, Andersen, R. et al. *Canc. Res.* 1989, 49, 5895-5900; cigarette smoke, Spiegelhalder, B. et al. *Euro. J. Canc. Prev.* 1996, 5, 1, 33-38; Hoffmann, D. et al. *J. Toxicol. Env. Hlth.* 1997, 50, 307-364; Borgerding, M. et al. *Food Chem. Toxicol.* 1998, 36, 169-182; nicotine-containing gum, Osterdahl, B.-G. *Food Chem. Toxic.* 1990, 28, 9, 619-622; and nicotine-containing transdermal patch, Adlkofer, F. In *Effects of Nicotine on Biological Systems II*, Clarke, P. et al. (Eds.); 1998, pp 17-25.

Green and freshly harvested tobaccos have reported to be virtually free of TSNAs. Parsons, A. *Tob. Sci.* 1986, 30, 81-82; Spiegelhalder, B. et al. *Euro. J. Canc. Prev.* 1996, 5, 1, 33-38; Brunnemann, K. et al. *J. Toxicol.-Clin. Toxicol.* 1982-3, 19, 6&7, 661-668; Andersen, R. et al. *J. Agric. Food Chem.* 1989, 37, 1, 44-50; Djordjevic, M. et al. *J. Agric. Food Chem.* 1989, 37, 752-756. However, it has been observed that TSNAs form during the post-harvest processing to which tobacco is subjected. Tricker, A. *Canc. Lett.* 1998, 42, 113-118; Chamberlain, W. et al. *J. Agric. Food Chem.* 1988, 36, 48-50. TSNAs are recognized as being formed when tobacco alkaloids, such as nicotine, are nitrosated. Hecht, S. Chem. Res. Toxicol. 1998, 11, 6, 559-603.

Significant efforts have been expended towards studying the mechanism of TSNA formation during tobacco curing. For example, it has been postulated that TSNAs form during the air-curing of Burley tobacco as a result of microbial mediated conversion of nitrate to nitrite, and the subsequent reaction of nitrate-derived chemical species with alkaloids present in the tobacco. Hamilton et al. *Tob. Sci.* 26, 133-137 (1982); Burton, H. et al. *J. Agric. Food Chem.* 1992, 40, 1050-1055; Bush et al., *Coresta Bulletin Information* 1995, Abstract, 9814; Wiernik, A. et al. *Rec. Adv. Tob. Sci.* 1995, 21, 39-80; Cui et al., *TCRC* (1996); deRoton, C. et al. *Beitrage Tabakforsch. Int.* 2005, 21, 6, 305-320; and Staaf, M. et al., *Beitrage Tabakforsch. Int.* 2005, 21, 6, 321-330. Additionally, for example, it has been postulated that TSNAs form during the flue-curing of Virginia tobaccos due to interaction of those tobaccos with nitric oxide combustion products present in exhaust gases produced during use of so-called direct-fired flue-curing barns. U.S. Pat. No. 7,404,406 to Peele and Nestor et al. *Beitrage Tabakforsch. Int.* 2003, 20, 467-475; see also U.S. Pat. No. 7,650,892 to Groves et al.

It would be desirable in the art to provide further methods for altering the character and nature of a plant such as a tobacco plant, as well as tobacco compositions and formulations useful in smoking articles or smokeless tobacco products.

SUMMARY OF THE INVENTION

The present disclosure provides a method of treating a plant or a portion thereof to modify (e.g., increase and/or decrease) the amount of certain bacteria present therein. Particularly, the disclosed methods can be applied to tobacco plants and materials and can, in some embodiments, result in a decrease in total bacterial content associated with the tobacco plant or material and/or an increase in *Lactobacillus* bacterial content associated with the tobacco plant or material.

In one aspect of the invention is provided a method of modifying the bacterial content of a tobacco material, comprising contacting an unharvested tobacco material up to about 24 hours before harvest with a treatment solution, wherein the treatment solution is selected from the group consisting of: (i) a solution comprising salt, sugar, or a combination thereof; (ii) a solution comprising one or more enzymes; and (iii) a solution comprising one or more probiotics, wherein said contacting provides a treated tobacco material having a reduced total bacterial content following harvest.

In certain embodiments, the treatment solution can comprise NaCl. In some embodiments, the treatment solution has a concentration of salt, sugar, or a combination thereof of between about 1 and about 4 percent by weight. The treatment solution can, in some embodiments, comprise *Lactobacillus* bacteria. For example, the treatment solution may comprise *Lactobacillus helveticus*. Where the treatment solution comprises probiotic bacteria, the treatment solution may, for example, have a concentration of probiotic bacteria of between about $1 \times 10^5$ colony forming units/mL and about $1 \times 10^{10}$ colony forming units/mL. Where the treatment solution comprises an enzyme, the treatment solution may, for example, have a concentration of enzyme of between about 10 AU and about 50,000 AU per plant.

In one embodiment, the method further comprises curing the treated tobacco material to give a treated, cured tobacco material. In certain embodiments, the tobacco-specific nitrosamine (TSNA) content of the treated, cured tobacco material is reduced relative to an untreated, cured tobacco material. In another aspect of the invention is provided a method of modifying the bacterial content of a tobacco material, comprising: contacting an unharvested tobacco material up to about 24 hours before harvest with a salt solution comprising NaCl in a concentration of about 0.5% to about 15% by weight of the treatment solution, wherein said contacting provides a treated tobacco material having a reduced total bacterial content following harvest; harvesting the treated tobacco material; and curing the harvested, treated tobacco material to give a treated, cured tobacco material.

The unharvested tobacco material can be, for example, selected from the group consisting of a tobacco seed, a tobacco seedling, an immature live plant, a mature live plant, or a portion thereof. In certain embodiments, the total bacterial content of the treated tobacco material is reduced by at least about 50% in number following harvest and in certain embodiments, the total bacterial content of the treated tobacco material is reduced by at least about 80% in number following harvest. In some embodiments, the total bacterial content of the tobacco material comprises Gramnegative bacteria and wherein the Gram-negative bacterial content of the treated tobacco material is reduced by at least about 50% in number following harvest. In some embodiments, the total bacterial content of the tobacco material comprises bacteria of the *Lactobacillus* genus, and wherein the *Lactobacillus* bacterial content of the treated tobacco material is increased following harvest.

One or more additional components can be added to the treatment solution. For example, the treatment solution can further comprise one or more surfactants. Various additional steps can be included in the methods provided herein. In some embodiments, the method can further comprise subjecting the treated, cured tobacco material to fermentation, wherein the fermentation is completed in less time than that required for fermentation of untreated, cured tobacco material. In some embodiments, the method can further comprise processing the treated, cured tobacco material to provide a processed tobacco material in a form suitable for incorporation in a tobacco product; and incorporating the processed tobacco material into a smokeless tobacco product or a smoking article. The processed tobacco material can be, for example, in the form of cut filler and/or a tobacco blend. In one embodiment, the method comprises contacting an unharvested tobacco material with a solution containing salt to give a treated tobacco material; harvesting and curing the treated tobacco material; subjecting the cured tobacco material to fermentation; and incorporating the fermented tobacco material into a smokeless tobacco product.

Tobacco products, in the form of smoking articles (e.g., cigarettes) or smokeless tobacco products, prepared according to the methods described herein, are also provided. In some embodiments, a smoking article produced according to the methods provided herein, upon smoking, is characterized by a TSNA content of mainstream smoke that is reduced relative to an untreated control smoking article.

In another aspect, the disclosure provides a method of reducing TSNA content of a tobacco material, comprising: growing a tobacco plant in soil treated with a chloride source; harvesting the tobacco plant; and curing the harvested tobacco plant to give a cured tobacco material, wherein said method provides a treated, cured tobacco material having a TSNA content that is reduced as compared to a cured tobacco material that has been grown in soil not treated with a chloride source.

In some embodiments, the method comprises planting tobacco prior to the soil treatment and in some embodiments, the method further comprises planting tobacco after the soil treatment.

In some embodiments, the method further comprises applying the chloride source to the soil. The chloride source can vary and can be, for example, a chloride salt (e.g., including but not limited to, sodium chloride (NaCl), potassium chloride (KCl), magnesium chloride ($MgCl_2$), calcium chloride ($CaCl_2$), and combinations thereof). In particular embodiments, the chloride source is KCl. In certain embodiments, the chloride source can be a compound capable of decomposition to provide chloride ions. In some embodiments, the chloride source can comprise one or more fertilizer components, selected from the group consisting of nitrogen, potassium, and phosphorus.

The chloride source can, in various embodiments, be applied in solid form or can be applied in the form of a solution of the chloride source. In some embodiments, the applying step can comprise applying the chloride in an amount of about 25 to about 150 lbs per acre.

The combined content of NNN, NAT, NAB, and NAK in the treated, cured tobacco material is advantageously low, for example, less than about 500 ng/g or less than about 200 ng/g. In certain embodiments, the NNN content in the treated, cured tobacco material can be less than about 100 ng/g or less than about 50 ng/g. In certain embodiments, the NAT content in the treated, cured tobacco material can be less than about 100 ng/g or less than about 75 ng/g. The combined NNN and NAT content can, in some embodiments, be less than about 150 ng/g.

In certain embodiments, the disclosed method provides a treated, cured tobacco material wherein the NNN content represents greater than a 50% reduction as compared with the NNN content of a cured tobacco material from a plant grown in soil with comparable levels of N, P, and K but without any chloride source added thereto. In certain embodiments, the disclosed method provides a treated, cured tobacco material wherein the NAT content represents greater than a 50% reduction as compared with the NAT content of a cured tobacco material from a plant grown in soil with comparable levels of N, P, and K but without any chloride source added thereto.

The curing can comprise, e.g., air curing or fire curing. In some embodiments, the method can further comprise processing the treated, cured tobacco material to provide a processed tobacco material in a form suitable for incorporation in a tobacco product; and incorporating the processed tobacco material into a smokeless tobacco product. The processed tobacco material may be, e.g., in the form of cut filler or in the form of a tobacco blend. In another embodiment, the disclosure provides a tobacco product in the form of a smokeless tobacco product prepared as described herein.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION OF THE INVENTION

Figure 1:
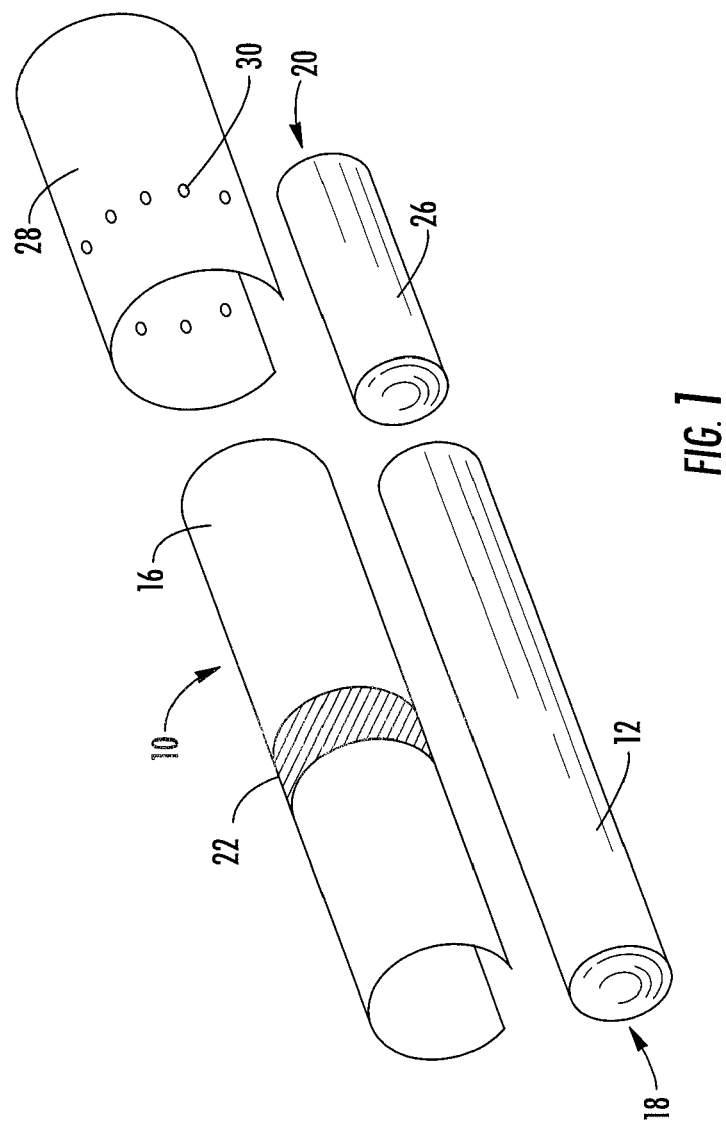
FIG. 1 is an exploded perspective view of a smoking article having the form of a cigarette, showing the smokable material, the wrapping material components, and the filter element of the cigarette.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The invention provides plants, plant components, and plant materials having modified levels of certain bacteria. In some embodiments, these plants, plant components, and plant materials having modified bacteria levels are subjected to curing and can exhibit modified levels of various compounds (e.g., tobacco-specific nitrosamines, TSNAs) post-curing. In one exemplary aspect, the invention provides tobacco plants, plant components, or tobacco materials having modified levels of certain bacteria and/or various compounds, tobacco products incorporating tobacco material derived from such tobacco, and methods for preparing a tobacco having modified levels of certain bacteria and/or compounds and for incorporating tobacco material derived from this tobacco within tobacco products.

The method of modifying levels of certain bacteria within tobacco materials generally comprises treating tobacco (in various forms, e.g., in unharvested or harvested form) by contacting the tobacco with one or more of: a salt and/or sugar solution; a probiotic solution; and/or an enzyme solution (collectively referred to herein as "treatment solutions"). It is noted that although the discussion provided herein focuses in large part on treatment of tobacco, a variety of other plants (including fruits, vegetables, flowers, and components thereof) can be treated according to the methods provided herein to afford plants, plant components, and materials and products produced therefrom having modified levels of certain compounds (e.g., bacteria) therein.

The tobacco can be treated in various stages of the plant life cycle, but typically is treated prior to or during the early phase of curing of the tobacco plant or plant component (i.e., the tobacco plant or plant component is "uncured or partially cured tobacco," which encompasses treatment prior to harvest and through the yellowing/browning phases of curing with the treatment solution). The yellowing/browning phase occurs during curing and describes a point at which the tobacco is harvested but has not undergone complete curing.

In certain preferred embodiments, the tobacco is treated prior to curing, i.e., in "green" form. By "green" in certain embodiments is meant tobacco having a form such that cells within the plant or plant component have not experienced significant or substantial cell death, and cellular respiration is capable of occurring to some degree. Although a tobacco material in "green" form can be in harvested or unharvested form, in certain embodiments, the tobacco material undergoing treatment as described herein is unharvested.

Accordingly, by "tobacco," "tobacco plant," or "tobacco plant components" is meant tobacco at various stages of the tobacco plant life cycle. For example, the tobacco plant component that is treated according to the present disclosure can be a tobacco seed, tobacco seedling, unharvested tobacco plant (at varying stages of maturity), harvested plant, or a portion of any of the above, which are all considered to be stages of the tobacco plant as described in further detail herein. In certain embodiments, the tobacco is treated prior to being dried (i.e., before harvest or just after harvest). In some embodiments, the tobacco is treated in a form wherein it is considered to be "alive." In certain embodiments, the tobacco is field-treated, meaning that the treatment is conducted on at least a portion of tobacco plants in unharvested form. In some embodiments, an unharvested tobacco plant that can be treated as described herein can be further described as growing in the field, having its roots in the ground, and continuing to go through the normal biological activity of a living organism.

In certain embodiments, the treatment can be performed within a specific time range prior to harvest. For example, in some embodiments, it may be beneficial to treat the tobacco less than about a week before harvest, including less than about 2 days before harvest or less than about 1 day before harvest. In certain embodiments, it may be advantageous to treat the tobacco a given number of hours before harvest, e.g., between about 1 and about 24 hours before harvest, between about 2 and about 12 hours before harvest, or between about 3 and about 10 hours before harvest. For example, the tobacco may be treated less than about 24 hours before harvest, less than about 15 hours before harvest, less than about 12 hours before harvest, less than about 10 hours before harvest, less than about 8 hours before harvest, or less than about 6 hours before harvest. In one embodiment, the tobacco is treated about 5 hours before harvest. Field treatment is particularly beneficial within a limited period of time before harvest, e.g., to avoid the diluting effects of rain and the possibly damaging effects of drying and UV radiation. It is noted that, in some embodiments, treatment may be conducted on an intact tobacco plant, whereas in other embodiments, treatment may be conducted on a plant having a portion removed therefrom (e.g., where the flower has been removed from the plant or where a portion of the leaves have been removed from the plant prior to treatment).

As noted above, the treatment solution can generally comprise one or more of: a salt and/or sugar solution; a probiotic solution; and/or an enzyme solution. Each of these types of treatment solutions will be described in greater detail herein. It is also to be understood that mixtures of such solutions can also be used in certain embodiments of the methods described herein (e.g., a probiotic-containing salt and/or sugar solution, an enzyme-containing salt and/or sugar solution, or a solution containing both an enzyme and a probiotic). The treatment solutions are generally described herein as being in liquid (solution) form. Although they are described as treatment "solutions," it is noted that some percentage of the solids can, in some embodiments, be incompletely dissolved (e.g., such that the "treatment solution" can be in solution, dispersion, or suspension form). The liquid with which the salt, sugar, enzyme, and/or probiotic is mixed can vary, but generally, the liquid will comprise water. Although in preferred embodiments, the solutions are aqueous solutions (i.e., comprising water), various other solvents (e.g., polar organic solvents such as methanol, ethanol, and propanol) can be used instead or in addition to the water. The concentration and amount of the salt, sugar, probiotic, or enzyme used can vary. Generally, the amount of the salt, sugar, probiotic, or enzyme is an amount sufficient to change the amount of one or more types of bacteria in the tobacco material to which it is applied. In other embodiments, application of the salt, sugar, probiotic, and/or enzyme can be performed with the salt, sugar, probiotic, and/or enzyme in a dry (e.g., freeze-dried) form. For example, methods analogous to those used in ensiling forage or dry salting can, in some embodiments, be used herein. See, for example, Stevens, H. R., *On Ensilage of Green Forage Crops in Silos;* 1881, which is incorporated herein by reference.

In embodiments wherein the treatment solution comprises a salt and/or sugar solution, the specific makeup of the solution can vary. In certain embodiments, the treatment solution may be such that it is hypertonic with respect to the plant or portion thereof subjected to treatment. A hypertonic solution is generally understood to be a solution with a high concentration of solute as compared with another solution, from which it is separated, e.g., by a semi-permeable membrane. Due to the higher concentration of solute on the hypertonic solution side of the membrane, fluid will generally flow across the membrane and into the hypertonic solution until an isotonic state is reached (wherein the solute concentrations on the two sides of the membrane are identical). In the context of the present application, a hypertonic solution is understood to be a solution wherein the solute or solutes in the solution are at a concentration that is higher than the concentration of that solute or solutes in the plant to be treated.

In certain embodiment, the treatment solution is a salt solution. Salt solution treatment of various types of plants is known, for example, as described in U.S. Pat. No. 6,755,200 to Hempffing et al. and US Pat. Appl. Publ. Nos. 2008/0202538 to Li et al. and 2012/0279510 to Marshall et al., which are all incorporated herein by reference. Any salt can be used for this purpose, although food-grade salts are especially preferred. Exemplary salts include, but are not limited to, sodium chloride (NaCl), calcium chloride ($CaCl_2$), magnesium chloride ($MgCl_2$), potassium chloride (KCl), and combinations thereof. In certain preferred embodiments, the treatment solution is a NaCl solution. In some embodiments, the salt solution is not a bicarbonate or carbonate anion-containing solution. The salt can be iodized or non-iodized (i.e., having a small amount of iodine added thereto), but preferably is non-iodized. The salt can be, for example, kosher salt, sea salt, or pickling salt. The particle size and shape of the salt can vary (e.g., the salt can be granulated, flaked, or powdered), so long as at least a portion of the salt particles are capable of being dissolved, e.g., in water, to form a solution.

In certain embodiments, the solute comprises sugar. Any sugar, including food-grade sugars, can be used for this purpose, e.g., including but not limited to, sucrose, glucose, fructose, galactose, maltose, and lactose, rhamnose, xylose, and combinations thereof. The form of sugar used according to the present disclosure can be, for example, powdered, crystalline, or syrup form, so long as at least a portion of the sugar is capable of being dissolved, e.g., in water, to form a hypotonic solution. In some embodiments, a solution comprising both salt and sugar can be used according to the method disclosed herein.

In embodiments wherein the treatment solution comprises a probiotic-containing solution, the solution can be, for example, as described in US Pat. Appl. Pub. No. 2013/0269719 to Marshall et al., which is incorporated herein by reference. Briefly, probiotic treatment comprises treatment with one or more "probiotics" or "probiotic microorganisms" which are intended to encompass all live microorganisms that may be classified as probiotics by various sources. For example, the Food and Agriculture Organization of the United Nations (FAO) defines probiotics as "live microorganisms, which, when administered in adequate amounts, confer a health benefit on the host." In some reports, such health benefits can include, but are not limited to: colonization of the intestinal, respiratory, and/or urogenital tracts, cholesterol metabolism, lactose metabolism, absorption of calcium, synthesis of vitamins, reduction of yeast and vaginal infections, reduction of digestive problems (e.g., constipation and diarrheal diseases), production of natural antibiotics, lactic acid, enzymes, hydrogen peroxide, inhibition of pathogenic microorganisms by production of antibiotic-like substances; and a decrease in pH. Although the traditional definition of "probiotic" relates to human and animal digestive organisms, this term has been applied in other contexts, such as in the field of agriculture. Exemplary probiotics include, but are not limited to, *bifidobacterium adolescentis, bifidobacterium animalis, bifidobacterium bifidum, bifidobacterium breve, bifidobacterium infantis, bifidobacterium lactis, bifidobacterium longum, bifidobacterium pseudocatenulatum, bifidobacterium pseudolongum, bifidobacterium sp., bifidobacterium thermophilum, lactobacillus acidophilus, lactobacillus alimentarius, lactobacillus amylovorus lactobacillus bulgaricus, lactobacillus bifidus, lactobacillus brevis, lactobacillus casei, lactobacillus caucasicus, lactobacillus crispatus, lactobacillus curvatus, lactobacillus delbruckii, lactobacillus fermentum, lactobacillus gallinarum, lactobacillus gasseri, lactobacillus helveticus, lactobacillus johnsonii, lactobacillus lactis, lactobacillus leichmannii, lactobacillus paracasei, lactobacillus plantarum, lactobacillus reuteri, lactobacillus rhamnosus, lactobacillus salivarius, lactobacillus sp., lactobacillus sporogenes, lactococcus lactis, streptococcus cermoris, streptococcus faceium, streptococcus infantis, streptococcus thermophilus, enterococcus faceium, pediococcus acidilactici, staphylococcus thermophilus, staphylococcus carnosus, staphylococcus xylosus, saccharomyces boulardii, saccharomyces cerevisiae, saccharomyces boulardii, bacillus cereus* var *toyo, bacillus subtilis, bacillus coagulans,* and *bacillus licheniformis*.

In embodiments wherein the treatment solution comprises an enzyme-containing solution, the solution can be, for example, as described in US Pat. Appl. Pub. No. 2014/0020694 to Moldoveanu et al., which is incorporated herein by reference. Briefly, enzymatic treatment comprises treatment with one or more enzymes, which as used herein, refers to any globular protein of varying size and structure. Generally, enzymes that are useful according to the invention function in some way to catalyze one or more chemical reactions within the plant material (e.g., by increasing the rate thereof). Any type of enzyme or combination of enzyme types can be employed according to the present invention; for example, hydrolases (which catalyze hydrolysis of chemical bonds), isomerases (which catalyze isomerizations within a molecule), ligases (which function to link two or more molecules), lyases (which cleave chemical bonds by mechanisms other than hydrolysis and oxidation), oxidoreductases (which catalyze oxidation/reduction reactions), and transferases (which transfer various moieties, e.g., functional groups). The origin of the enzymes can vary and the enzymes can be obtained, for example, from microbial sources (e.g., bacterial sources or fungal sources), plant sources, animal sources, and/or can be synthetically produced. Exemplary enzymes include, but are not limited to, amylases (e.g., α-amylase, β-amylase, γ-amylase, or a combination thereof) and/or proteases (e.g., serine proteases, threonine proteases, cysteine proteases, asparatate proteases, metalloproteases, and glutamic acid proteases including protease *bacillus licheniformis*, protease *bacillus* sp., protease *Aspergillus oryzae*, protease *bacillus amyloliquefaciens*, protease *bacillus*, and protease *Streptomyces griseus*). In certain embodiments, the one or more enzymes comprise asparaginase (e.g., PreventASe™, DSM Food Specialties, Heerlen, NL and Acrylaway®, Novozymes, A/S, Bagsvaerd, DK). In certain embodiments, the one or more enzymes comprise a polyphenol oxidase (PPO). In some embodiments, the one or more enzymes comprise an oxidase such as a monophenol oxidase enzyme (tyrosinase) or an o-diphenol oxygen oxidoreductase enzyme (catechol oxidase). Another exemplary oxidase is laccase.

The solute of the treatment solution (i.e., the salt(s), sugar(s), probiotics, enzymes, or combination thereof) can be present in varying concentrations. Generally, a somewhat dilute solution is used according to the methods provided herein, although the concentration can be any concentration sufficient to elicit the desired effect in the treated tobacco plant.

For example, in some embodiments, salt, sugar, or a combination thereof is present in a concentration of about 0.5% to about 15% by weight of the treatment solution, about 0.5% to about 10%, or about 1% to about 5% by weight of the treatment solution (e.g., about 1.5%, about 2%, about 2.5%, or about 3% by weight of the treatment solution).

In some embodiments, the treatment solution comprises a probiotic in an amount of between about $1 \times 10^5$ colony forming units (CFU)/mL and about $1 \times 10^{10}$ CFU/mL (e.g., about $2 \times 10^6$ CFU/mL). CFU provides a measurement of viable (living) cells in the probiotic sample.

In some embodiments, the treatment solution comprises an enzyme in an amount of between about 10 and about 50,000 active units (AU) per plant. For example, exemplary amounts of the enzyme can be between about 100 and about 10,000 AU per plant, e.g., between about 500 and about 5,000 AU per plant (typical AU level for a commercial product PreventASe™ L (from DSM) is 2,600 AU/mL for the preparate of asparaginase). For dry tobacco (~12% moisture), a range between 20 and 100 AU/g can be used. In embodiments wherein the enzyme comprises commercial polyphenol oxidase (PPO), between about 100 and about 10,000 AU per plant, e.g., between about 1,000 and about 5,000 AU per plant can be used (typical AU level for a commercial product (from Worthington) is 1,000 AU/mL for the preparate).

In certain embodiments, other components can be applied to the plant with the treatment solution. Such components can be added within the same formulation (e.g., within the same solution, dispersion, suspension) or can be applied to the tobacco in a separate formulation. For example, in some embodiments, one or more surfactants and/or detergents are applied to the tobacco with the sugar, salt, enzyme, and/or probiotic. The surfactants can be, for example, non-ionic surfactants. Various surfactants can be used, including, but not limited to, polysorbate surfactants, such as polysorbate 20 (Tween-20®) and polysorbate 80 (Tween-80®) and poly (ethylene glycol)-based surfactants, such as Triton™ X Series surfactants. Other reagents for helping the treatment solution coat the tobacco effectively can include various sugars, plant extracts (e.g., yucca extracts, seaweed extracts), and derivatives thereof. Certain enzymes and probiotics are active only within a particular pH range; therefore, use of pH adjusters, acids, bases, and/or buffers may be beneficial in the application of certain treatment solutions. In some embodiments, the treatment solution may contain one or more amino acids (e.g., lysine, glycine, histidine, alanine, methionine, glutamic acid, aspartic acid, proline, phenylalanine, valine, and arginine), compositions incorporating cations (e.g., di- and/or trivalent cations), certain non-reducing saccharides, certain reducing agents, phenolic compounds (e.g., compounds having at least one phenolic functionality), certain compounds having at least one free thiol group or functionality, oxidizing agents (e.g., hydrogen peroxide or ozone), oxidation catalysts (e.g., titanium dioxide), natural plant extracts (e.g., rosemary extract), and combinations thereof. The amount of the one or more other components that can optionally be added to the plant with the treatment solution can vary. For example, in certain embodiments, the treatment solution may comprise up to about 25% by weight of the treatment solution, e.g., between about 1 and about 20% by weight.

As noted above, the treatment can comprise treating the tobacco material (e.g., green tobacco plant material) with one or more of the types of treatment solutions described herein. Such treatments can, in some embodiments, comprise treating the tobacco with two or more different types of treatment solutions sequentially (e.g., in close succession or at significantly different time points) or simultaneously (e.g., by separately applying two or more different solutions to the tobacco or by mixing the solutions to provide a single treatment solution comprising two or more different solutes and applying the single treatment solution to the tobacco). Tobacco can be treated with a treatment solution (i.e., a salt and/or sugar solution; a probiotic solution; and/or an enzyme solution) once or can be treated multiple times. In some embodiments, two treatment solutions, which may be the same or different, can be provided in separate formulations and applied at different points of the tobacco plant life cycle (e.g., with one applied to growing plants in the field and one applied following harvest or with one applied to seeds and one applied to growing plants in the field).

Treatment of tobacco with a treatment solution according to the methods provided herein can have varying effects on the resulting treated tobacco. It is noted that the specific results obtained may be related, at least in part, to the specific type of salt(s), sugar(s), enzyme(s), and/or probiotic(s) that are used in the treatment.

For example, in certain embodiments, tobacco treated with a salt and/or sugar solution; a probiotic solution; and/or an enzyme solution can exhibit modified levels of certain bacteria associated therewith. It is known that tobacco plants naturally have various levels of bacteria associated therewith. See, for example, Larsson L. et al. *Tobacco Induced Diseases* 2008, 4, 4 and Huang, J. et al. *Appl. Microbiol. Biotechnol.* 2010, 88, 2, 553, which are incorporated herein by reference.

"Bacteria" is generally understood to refer to a genus of prokaryotic microorganisms scientifically classified as such. Most bacteria can be classified as Gram-positive (classified principally in the phylum "Actinobacteria") or Gram-negative (classified principally in the phylum "Proteobacteria"). "Gram-negative" as referred to herein relates to bacteria bounded by a cytoplasmic membrane as well as an outer cell membrane, containing only a thin layer of peptidoglycan between the two membranes, which is unable to retain crystal violet stain in a Gram staining technique (whereas Gram-positive bacteria are bounded by only a single unit lipid membrane and contain a thick layer (20-80 nm) of peptidoglycan, which retains the stain). Exemplary Gram-negative bacteria include, but are not limited to, proteobacteria (e.g., from the genera Enterobacteriaceae (including *Escherichia, Salmonella, Shigella, Serratia, Pantoea, Proteus,* and *Klebsiella*), Pseudomonaceae (including *Pseudomonas* and *Rhizobacter*), Moraxellacae (e.g., *Moraxella* and *Acinetobacter*), Helicobacteracae (e.g., *Helicobacter*), Xanthomonadacae (e.g., *Stenotrophomonas* and *Xanthomonas*), Bdellovibrionacaea (e.g., *Bdellovibrio*), Burkholderiaceae (e.g., *Burkholderia*), Legionellaceae (e.g., *Legionella*), Rhizobiaceae (e.g., *Agrobacterium*); Acetobacteraceae (e.g., acetic acid bacteria), Spirillaceae (e.g., *Spirillum*), and Campylobacteraceae (e.g., *Campylobacter*)). In some embodiments, certain bacteria associated with tobacco plants are anaerobic microorganisms.

Enteric bacteria are gram-negative, anaerobic bacteria of the family Enterobactericeae that are commonly found in the gut of animals, including humans. Over 40 genera have been identified in this family, including *Salmonella, Proteus, Serratia, Enterobacter, Citrobacter, Pseudomonas,* and *Klebsiella*. Other bacterial types typically found in the gut of animals can also be considered enteric bacteria, e.g., bacteria belong to the genera *Bacteroides, Clostridium, Fusobacterium, Eubacterium, Ruminococcus, Peptidococcus, Peptostreptococcus, Eschericia,* and *Bifidobacterium*. Various tests to quantify enteric bacteria may also quantify certain other gram negative bacteria in addition to Enterobactericeae (e.g., *Salmonella* and *Eschericia*). Although some of these bacteria can live in the gut without health problems, some can are opportunistic pathogens and/or cause signs of infection, and the presence of such bacteria is thus often advantageously minimized.

*Lactobacillus* is a specific large genus of gram-positive rod-shaped bacteria that produce lactic acid. Many bacteria in this genus are beneficial (and thus commonly used in probiotic preparations).

In some embodiments, the treatment described herein results in a treated tobacco plant material having a modified total bacteria count, a modified enteric bacteria count, a modified gram-negative bacteria count, and/or a modified *Lactobacillus* count. Although not intended to be limiting, it is believed that, in some embodiments, sugar and/or salt solutions can modify the bacteria count by creating a hypertonic solution with respect to the tobacco material and that probiotics and/or enzymes can modify the bacteria count by providing a competitive bacterial load per unit area associated with the tobacco material.

In certain embodiments, treatment as described herein provides a treated tobacco plant material with a modified total bacteria count and, specifically, may provide an overall reduction in total bacteria count. A total bacteria count can be conducted using any method known in the art, e.g., by diluting a sample and plating the diluted sample(s) on a growth medium (e.g., plate count agar, PCA). The plate is then incubated, and each bacterium present in the sample is expected to grow into an individual colony on the plate. The resulting colonies can be viewed (e.g., under a microscope) and counted to provide a total bacterial count in colony forming units/gram (CFU/g). Other methods include, but are not limited to, using counting chambers, using membrane filters that are capable of retaining bacteria, photometry and/or spectroscopy (e.g., turbidimetric analysis). The reduction in the total bacteria count following treatment with one or more of: a salt and/or sugar solution; a probiotic solution; and/or an enzyme solution can be, for example, a reduction of greater than about 80%, greater than about 85%, greater than about 90%, greater than about 92%, greater than about 95%, or greater than about 96%, based on total bacterial counts (obtained, e.g., by taking colony forming units/gram of a treated tobacco sample, dividing it by colony forming units/gram of an untreated tobacco sample, subtracting the resulting number from 1, and multiplying by 100).

It is understood that some percentage of the total bacteria present on the tobacco plant material prior to treatment will comprise gram negative bacteria. Therefore, it follows that, following treatment, the tobacco plant material may generally exhibit a modified gram-negative bacteria count and, specifically, may exhibit an overall reduction in gramnegative bacteria count. In some embodiments, the decrease in gram-negative bacteria can be quantified by evaluating the total bacteria count as described above before and after treatment using a method specific for gram-negative (as opposed to gram-positive) bacteria. Such a method can, in some embodiments, comprise gram staining, observing the bacteria under a microscope, rapid microbial identification systems, and/or polymerase chain reaction (PCR) protocols.

In certain embodiments, treatment as described herein provides a tobacco plant material with a modified enteric bacteria count and, specifically, may provide a plant material with an overall reduction in enteric bacteria count. Enteric bacteria count can be quantified, for example, by the total bacterial count method described above, wherein the bacteria are grown on a selective medium rather than a general bacterial growth medium (e.g., a violet red bile agar (VRBA) plate rather than a plate count agar (PCA) plate). The reduction in the enteric bacteria count following treatment with one or more of: a salt and/or sugar solution; a probiotic solution; and/or an enzyme solution can be, for example, a reduction of greater than about 80%, greater than about 85%, greater than about 90%, greater than about 92%, greater than about 95%, or greater than about 96%, based on total bacterial counts (obtained, e.g., by taking colony forming units/gram of a treated tobacco sample, dividing it by colony forming units/gram of an untreated tobacco sample, subtracting the resulting number from 1, and multiplying by 100).

In certain embodiments, treatment as described herein provides a modified *Lactobacillus* bacteria count and, specifically, may provide an overall increase in *Lactobacillus* bacteria count. *Lactobacillus* counts can be obtained, for example, using the count method described above on a medium specific for *lactobacillus* (e.g., deMan Rogosa and Sharpe (MRS) medium). The MRS medium may allow for the growth of certain other types of bacteria in addition to *Lactobacilli* and thus "modified *lactobacillus* bacteria count" in certain embodiments refers to a count of all bacteria that grows on MRS media under anaerobic conditions, e.g., which in addition to *Lactobacilli* may include *Leuconostoc* and *Pediococcus*. The increase in the *Lactobacillus* bacteria count following treatment with one or more of: a salt and/or sugar solution; a probiotic solution; and/or an enzyme solution can be, for example, an increase of greater than about 50%, greater than about 100%, greater than about 150%, greater than about 200%, greater than about 300%, or greater than about 400%, based on total bacterial counts (obtained, e.g., by taking colony forming units/gram of a treated tobacco sample, dividing it by colony forming units/gram of an untreated tobacco sample, subtracting the resulting number from 1, and multiplying by 100). It is noted that, although an increase in *Lactobacillus* count is desirable in certain embodiments, some treatments result in a decrease in *Lactobacillus* count (e.g., providing a reduction in *Lactobacillus* count of treated tobacco of between about 0% and about 50% in some embodiments).

Different treatments can have different effects on the levels of various bacteria present within the tobacco plant material. As noted above, the treatment described herein may affect the properties of the treated tobacco and may be particularly beneficial to modify the content of certain bacteria prior to curing the treated tobacco. The pre-cure treatment disclosed herein can, in some embodiments, have further implications for later processing steps.

In the production of tobacco products, tobacco material is often cured and/or aged in order to convert the tobacco to a consumable form. Curing may comprise, for example, putting harvested tobacco material in an enclosure (e.g., a barn), under conditions allowing for oxidation and degradation of certain tobacco components. Curing typically dries the tobacco and commonly results in changes to the overall chemistry of the tobacco.

Examples of methods for curing and/or aging tobacco are discussed, for example, in U.S. Pat. No. 1,327,692 to Beinhart; U.S. Pat. No. 2,758,603 to Heljo; U.S. Pat. No. 5,676,164 to Martin; U.S. Pat. No. 6,755,200 to Hempfling et al.; U.S. Pat. No. 7,293,564 to Perfetti et al., and U.S. Pat. No. 8,353,300 to Li et al.; and US Pat. Appl. Pub. Nos. 2010/0116281 and 2012/0279510 to Marshall et al., which are incorporated herein by reference in their entireties.

Descriptions of further types of curing and aging processes for various types of tobacco are provided in Tobacco Production, Chemistry and Technology, Davis et al. (Eds.) (1999), which is also incorporated herein by reference.

For example, tobacco can be cured by methods including but not limited to, air-curing, dark air curing, sun-curing, fire curing, and flue curing. Flue curing comprises curing tobacco in enclosures wherein flues heat cure the tobacco without exposing it to smoke and is described, for example, in Nestor et al. *Beitrage Tabakforsch. Int.*, 2003, 20, 467-475 and U.S. Pat. No. 6,895,974 to Peele, which are both incorporated herein by reference. Fire cured tobacco generally comprises curing tobacco in enclosures wherein it is exposed to the gaseous combustion products of a fire that is maintained at a low smolder and is described, for example, in US Pat. Appl. Publ. 2012/0125354 to Byrd et al., which is incorporated herein by reference. Air curing typically comprises hanging tobacco in a well-ventilated enclosure to dry at ambient conditions and is described, for example, in deRoton, C. et al. *Beitrage Tabakforsch. Int.* 2005, 21, 6, 305-320; Staaf, M. et al. *Beitrage Tabakforsch Int.* 2005, 21, 6, 321-330; and U.S. Pat. No. 6,834,654 to Williams, which are incorporated herein by reference. Sun curing generally comprises allowing tobacco to cure uncovered in the sun.

The tobacco material comprising modified bacteria levels (provided via treatment as described herein) can lead to modified levels of other types of compounds in the tobacco material after curing as compared with untreated tobacco material after curing. Such compounds may, in certain embodiments, be smoke toxicants and/or smoke toxicant precursors. For example, it is believed that certain compounds are produced, at least in part, by the action of bacteria (e.g., gram negative bacteria) during the curing process. Specifically, bacteria can produce the enzyme nitrate reductase, which converts nitrates to nitrite and nitric oxide; nitric oxide can subsequently react with precursor tobacco alkaloids to produce tobacco-specific nitrosamines (TSNAs). Exemplary TSNA compounds include N-nitrosonornicotine (NNN), 4-methyl-N-nitrosamino-1-(3-pyridyl)-1-butanone (NNK), N-nitrosoanatabine (NAT), 4-methyl-N-nitrosamino-1-(3-pyridyl)-1-butanol (NNAL), and N-nitrosoanabasine (NAB).

Although low levels of TSNA are typically observed in green tobacco material, it is generally understood that TSNAs are formed during tobacco curing, fermentation, and/or aging processes. Consequently, various efforts to reduce TSNA levels by modifying the growth or curing process have been attempted. See, for example, U.S. Pat. Nos. 4,343,317 and 4,347,859 to Bokelman; U.S. Pat. No. 5,803,081 to O'Donnell; U.S. Pat. No. 6,202,649 to Williams; U.S. Pat. No. 6,805,134 to Peele; U.S. Pat. No. 7,293,564 to Perfetti et al.; U.S. Pat. No. 7,404,406 to Peele; U.S. Pat. No. 8,353,300 to Li et al.; US Pat. Appl. Publ. No. 2012/0234334 to Chen et al.; PCT Appl. Publ. Nos. WO 83/01180 to Malik; WO 98/05226 and WO 98/58555 to Williams; and WO 01/35770 and WO 02/13636 to Hempfling et al., WO 03/094639 to Koga et al., and Müller et al. *Molec. Gen. Genet.* 1987, 161, 67-76, which are all incorporated herein by reference.

Accordingly, modifying the level of bacteria (e.g., gram negative bacteria) generally associated with tobacco material subjected to curing can, in some embodiments, lead to a cured tobacco material having a modified level of TSNAs (e.g., fewer TSNAs by weight than in a comparable tobacco material that has not been treated prior to curing as described herein). In certain embodiments of the invention, the decrease in the level of TSNAs can vary but generally, a treated, cured tobacco will comprise between about 10% and about 90% by weight of TSNAs generally as compared with the amount of TSNAs present in a comparable cured (but untreated) tobacco. For example, in certain embodiments, treated tobacco material may exhibit at least a 10%, 20%, 30%, 40%, 50%, 60%, 70%, or 80% decrease in TSNA compounds by weight after curing as compared with an untreated tobacco material after curing.

As described herein, treatment of a tobacco material with a treatment solution comprising a salt and/or sugar solution; a probiotic solution; and/or an enzyme solution can, in some embodiments, result in a modified (e.g., increased) number of *Lactobacillus* bacteria associated with the treated tobacco material relative to untreated tobacco material. This possible increase in *lactobacilli* associated with treatment of tobacco materials as described herein can, in some embodiments, have further beneficial effects. In certain embodiments (e.g., where tobacco material is being prepared for use in certain smokeless tobacco products), the tobacco material is cured and then fermented.

Fermentation generally requires subjecting the tobacco material to water (e.g., humidity) and heat. The fermentation process can be conducted in a chamber where the temperature and moisture content can be controlled. As a consequence of the elevated temperature and moisture content to which the tobacco is exposed during the fermentation process, certain components (e.g., ammonia) may be effectively removed from the tobacco. In some embodiments, fermentation is a bacterial process, wherein certain bacteria produce enzymes that react to produce flavor precursors within the fermenting tobacco material.

Exemplary fermentation processes for tobacco are provided in U.S. Pat. No. 2,927,188 to Brenik et al.; U.S. Pat. No. 4,660,577 to Sensabaugh et al.; U.S. Pat. No. 4,528,993 to Sensabaugh et al.; and U.S. Pat. No. 5,327,149 to Roth et al., which are incorporated herein by reference. Fermentation is enhanced by the presence of *Lactobacillus*; consequently, modification of the amount of *Lactobacillus* bacteria associated with a given tobacco sample can impact the fermentation of that tobacco sample. Where that treated tobacco is later subjected to fermentation, the fermentation can, in some embodiments, be enhanced by the presence of a greater number of *Lactobacillus* bacteria. By "enhanced" is meant that the fermentation process proceeds, for example, more quickly, and/or more uniformly.

Tobacco or tobaccos to which the method provided herein is applicable can vary. In certain embodiments, tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Pasado, Cubano, Jatim and Bezuki tobaccos), light air cured (e.g., North Wisconsin and *Galpao* tobaccos), Indian air cured, Red Russian and *Rustica* tobaccos, as well as various other rare or specialty tobaccos and various blends of any of the foregoing tobaccos. Descriptions of various types of tobaccos, growing practices and harvesting practices are set forth in *Tobacco Production, Chemistry and Technology*, Davis et al. (Eds.) (1999), which is incorporated herein by reference. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al. and U.S. Pat. No. 7,025,066 to Lawson et al.; US Patent Appl. Pub. Nos. 2006/0037623 to Lawrence, Jr. and 2008/0245377 to Marshall et al.; each of which is incorporated herein by reference. Exemplary *Nico-

*tiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia,* and *N. spegazzinii.*

*Nicotiana* species can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO 2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference. Most preferably, the tobacco materials are those that have been appropriately cured and aged. Especially preferred techniques and conditions for curing flue-cured tobacco are set forth in Nestor et al., Beitrage Tabakforsch. Int., 20 (2003) 467-475 and U.S. Pat. No. 6,895,974 to Peele, which are incorporated herein by reference. Representative techniques and conditions for air curing tobacco are set forth in deRoton, C. et al. *Beitrage Tabakforsch. Int.,* 2005, 21, 6, 305-320 and Staaf, M. et al. *Beitrage Tabakforsch. Int.* 2005, 21, 6, 321-330, which are incorporated herein by reference. Certain types of unusual or rare tobaccos can be sun cured. Manners and methods for improving the smoking quality of Oriental tobaccos are set forth in U.S. Pat. No. 7,025,066 to Lawson et al., which is incorporated herein by reference. Representative Oriental tobaccos include katerini, prelip, komotini, xanthi and yambol tobaccos. Tobacco compositions including dark air cured tobacco are set forth in US Patent Appl. Pub. No. 2008/0245377 to Marshall et al., which is incorporated herein by reference. See also, types of tobacco as set forth, for example, in US Patent Appl. Pub. No. 2011/0247640 to Beeson et al., which is incorporated herein by reference.

The *Nicotiana* species can be selected for the content of various compounds that are present therein. For example, in certain embodiments, plants of the *Nicotiana* species (e.g., *Galpao commun* tobacco) are specifically grown for their abundance of leaf surface compounds. In certain embodiments, plants of the *Nicotiana* species are specifically grown for their relatively low levels of certain undesired compounds (e.g., asparagine). Tobacco plants can be grown in greenhouses, growth chambers, or outdoors in fields, or grown hydroponically.

The means by which the treatment solutions described herein can be applied to the tobacco plant or plant material can vary. Certain methods to treat plants with a salt and/or sugar solution, probiotic solution, and/or an enzyme solution which could be used or modified for use, in the present invention are provided in U.S. Pat. No. 4,140,136 to Geiss et al.; U.S. Pat. No. 4,151,848 to Newton et al.; U.S. Pat. No. 4,308,877 to Mattina et al.; U.S. Pat. No. 4,476,881 to Gravely et al.; U.S. Pat. No. 4,556,073 to Gravely et al.; U.S. Pat. No. 4,557,280 to Gravely et al.; U.S. Pat. No. 4,566,469 to Semp et al.; U.S. Pat. No. 5,372,149 to Roth et al.; U.S. Pat. No. 7,549,425 to Koga et al.; U.S. Pat. No. 7,549,426 to Koga et al.; and U.S. Pat. No. 7,556,046 to Koga et al., all of which are incorporated herein by reference.

The method of application of the treatment solution as disclosed herein will often depend, at least in part, on the stage of the tobacco plant. For example, in certain embodiments, the salt and/or sugar solution; probiotic solution; and/or enzyme solution are applied to a tobacco seed prior to planting. In such embodiments, the treatment solution can be applied in the form of a seed treatment or coating. For example, the seeds can be dipped in such a solution, soaked in the solution, or sprayed with the solution. In certain embodiments, the solution can be applied to a tobacco in seedling or unharvested (live) plant form or may be applied to the soil in which the tobacco plants will be planted or are presently planted. In such embodiments, spray application of treatment solution can be used (e.g., using a hydraulic boom sprayer, air blast sprayer, sprinkler system, fogger, or aerial sprayer), although the method of application is not limited thereto. Certain methods to treat plants with microorganisms which could be used, or modified for use, in the present invention are provided in U.S. Pat. No. 4,140,136 to Geiss et al.; U.S. Pat. No. 4,151,848 to Newton et al.; U.S. Pat. No. 4,308,877 to Mattina et al.; U.S. Pat. No. 4,476,881 to Gravely et al.; U.S. Pat. No. 4,556,073 to Gravely et al.; U.S. Pat. No. 4,557,280 to Gravely et al.; U.S. Pat. No. 4,566,469 to Semp et al.; U.S. Pat. No. 5,372,149 to Roth et al.; U.S. Pat. No. 7,549,425 to Koga et al.; U.S. Pat. No. 7,549,426 to Koga et al.; and U.S. Pat. No. 7,556,046 to Koga et al., all of which are incorporated herein by reference.

Although it may be advantageous to apply the treatment (i.e., solution containing salt and/or sugar, probiotic(s), and/or enzyme(s)) while the tobacco plant is still in living form, it is also possible in some embodiments to apply the treatment solution following harvesting of the tobacco plants. Such application can occur at any time following harvest, including immediately following harvest, prior to or following post-harvest processing (e.g., drying, curing, and/or physical processing of the plant), or at any stage in between. Advantageously, the treatment is conducted prior to any significant curing of the tobacco plant material. The application of salt and/or sugar solution, probiotic solution, and/or enzyme solution can be done at one stage in the plant life cycle, or can be conducted at two or more stages.

In one particular embodiment, the tobacco plant (or soil in which tobacco plants will be planted or are presently planted) is treated with a chloride source, e.g., a chloride salt. Specific chloride salts that can be used can vary and can include, but are not limited to, sodium chloride (NaCl), potassium chloride (KCl), magnesium chloride ($MgCl_2$), calcium chloride ($CaCl_2$), ammonium chloride ($NH_4Cl$), and combinations thereof. In addition to salts, in some embodiments, chlorine-containing compounds capable of decomposition to produce chloride ions under typical field conditions can be employed. In some embodiments, the tobacco plant is described as being grown, at least partially, in a high salt medium, e.g., soil of elevated salinity. Accordingly, although treatment of plants and/or soil is disclosed herein as a means for providing the tobacco plant with a chloride source, it is to be understood that in other embodiments, tobacco plants may be grown, at least in part, in a soil that already has sufficient salt content/salinity (e.g., including, but not limited to, soil near the ocean or other marshy, salt water areas).

According to the present disclosure, growing tobacco plants at least partially in a chloride-containing environment (e.g., by treating a tobacco plant during growth with chloride ions as described herein) can lead to reductions in the later formation of TSNAs that is typically observed, e.g., during tobacco curing processes. The exact mechanism by which the disclosed chloride treatment effects this reduced TSNA content in tobacco plants is not known. However, it is believed that the exposure of tobacco plants to increased levels of chloride ions can create an environment that inhibits the formation of TSNAs.

Formation of TSNAs during air curing is understood to arise, at least in part, from increasing bacteria levels during the curing process. As described herein, increasing the amount of chloride associated with the tobacco material prior to curing may be decreasing TSNA formation by affecting this increase in bacteria level and/or by modifying the content of certain bacteria strains (e.g., those resistant to salt). Information on bacterial communities present in certain smokeless tobacco products (the content of which may, in some embodiments, be modified according to the methods disclosed herein) are described, for example, in Tyx, R. et al. *Plos ONE* 2016, 11, 1, e0146939, which is incorporated herein by reference. Advantageously, it is believed that growing tobacco plants in a chloride-containing environment may serve to inhibit the later increase in bacteria level commonly observed during air curing of the tobacco material, such that the air cured tobacco material treated with a chloride source prior to curing (e.g., by treating the plant during growth or the soil in which it is grown) exhibits a bacterial content that is reduced and/or a bacterial profile that is modified as compared with air cured tobacco material that has not been treated in such a manner.

Formation of TSNAs during fire curing is understood to arise, at least in part, from reaction of nitrous oxides typically generated during the curing process. According to the methods disclosed herein, growing tobacco plants, at least partially, in a chloride-containing environment can, in some embodiments, serve to modify the extent of such later reactions, thus affecting the TSNA content of the cured material.

In certain embodiments, the chloride source can have multiple functions in addition to serving as a source of chloride. For example, in some embodiments, the chloride source may also function to provide fertilization to the plant. In one embodiment, tobacco plants (or soil in which the plants will be planted or are presently planted) is treated with KCl. Traditionally, tobacco is fertilized with a potassium-containing fertilizer (e.g., potassium sulfate). By replacing at least a portion of the potassium-containing fertilizer with KCl, a desired fertilizing effect may be achieved while also providing a chloride source. In other embodiments, the chloride source may be in the form of a nitrogen fertilizer or phosphorus fertilizer to provide such multiple functions with respect to the growth of the tobacco plant. Examples of fertilizers, and in particular, chloride-containing fertilizers, and representative methods for treatment of crops using such fertilizers are found in Grant, C. A., Advanced Silage Corn Management 2004, Chapter 3, which is incorporated herein by reference in its entirety.

It is noted that application of chloride-containing reagents (e.g., chloride salts) to tobacco plants (or soil in which tobacco plants will be planted or are presently planted) is typically avoided. Treatment of tobacco plants with chloride (e.g., chloride-containing salts) has been noted to lead to poor burning and poor smoke flavor in cigarettes produced from such tobacco plants. However, for certain applications, e.g., in smokeless tobacco products, the presence of chloride (e.g., chloride salt) in tobacco plants may not be disadvantageous and may, in fact, be beneficial (e.g., due to decreased TSNA content after curing, as described in further detail herein). Further, in the context of smoking products, treatment with a chloride source can be advantageous for, e.g., decreasing TSNA content after curing where the chloride (e.g., salt) can be effectively removed from the tobacco material after curing.

Accordingly, in some embodiments, the chloride source can be applied (to the tobacco plants or the soil) at a rate higher than that typically understood to be acceptable for tobacco plants. For example, the chloride source can, in some embodiments, be applied such that the chloride is present in about 25 pounds per acre or more, about 50 pounds per acre or more, or about 75 pounds per acre or more. Where the chloride source is provided in the form of a fertilizer material (e.g., KCl), it is noted that the chloride source can be provided in an amount sufficient to fulfill the fertilizing function. In some such embodiments, KCl can be applied in an amount sufficient to provide the desired potassium level for fertilization. In other embodiments, KCl can be applied in an amount below that sufficient to provide the desired potassium level for fertilization and, accordingly, a second potassium source may, in such embodiments, be employed in combination with KCl.

The chloride source can be applied in various forms as outlined herein (e.g., in the form of solutions of varying concentrations and solid form). In certain preferred embodiments, the chloride source can be applied as a solid, e.g., using techniques common in fertilizer application (including, but not limited to, broadcast application, top-dressing, side-dressing, or foliar feeding, e.g., by application of the chloride in solution form). Where the chloride source is applied to soil, it may be advantageous to incorporate the chloride source into the soil (e.g., by ensuring that it becomes mixed with the soil, rather than sitting on top of the soil). The chloride source can be applied to the tobacco plant or soil alone or in combination with one or more other components (e.g., one or more fertilizers). The timing of application can vary. As noted, in some embodiments, the soil is treated with a chloride source prior to planting of tobacco plants; tobacco seeds or plants at various stages of growth can subsequently be placed in the soil. In such embodiments, the tobacco plants or seedlings can be initially grown by any means, e.g., including in typical soil as used in fields and in greenhouses or other types of growth media, including under hydroponic conditions.

In other embodiments, the soil or tobacco plant is treated with a chloride source in situ, i.e., when the tobacco is planted in the ground. The chloride treatment can be conducted in such embodiments, e.g., where the tobacco plant is still in seed/seedling form or where the tobacco plant is in immature or mature plant form. Particular time ranges for application of such components to tobacco plants with respect to the time of harvest are provided in greater detail herein. In some embodiments, it may be advantageous to apply the chloride treatment, e.g., to soil just prior to transplanting tobacco plants therein or after transplanting tobacco plants therein to prevent leaching of significant amounts of chloride ions, e.g., due to rainfall. It is noted that in some embodiments, it may be advantageous to ensure that chloride treatment is applied at an appropriate time and in an appropriate manner, e.g., such that germination is not prevented and such that significantly stunted growth of the tobacco plant is not observed following treatment.

Various types of tobacco plants can be treated with a chloride source, as generally described herein and such treatment can be effective for reducing TSNA content as measured following various types of curing methods, as also generally described herein. In some embodiments, such treatment may be particularly relevant for air cured (e.g., dark air cured) tobacco and fire cured (e.g., dark fire cured) tobacco.

The extent of TSNA reduction that can be provided by the application of a chloride source to a tobacco plant or the soil in which it is grown or will be grown can, in some embodiments, be significant. In certain embodiments, the total TSNA level of tobacco material treated as described herein above by application of a chloride source can, after the tobacco material is cured, be less than about 2,000 ng/g, less than about 1,000 ng/g, less than about 500 ng/g, less than about 250 ng/g, or less than about 200 ng/g. In some embodiments, the total level of NNN, NAT, NAB, and NNK is within the noted ranges. In some embodiments, the level of NNN and/or NAT in the cured tobacco material is particularly low, e.g., as compared with a similar cured tobacco material that has not been subjected to treatment with a chloride source.

For example, the NNN content of cured tobacco material that has been treated with a chloride source prior to harvest, as provided herein, can in some embodiments be less than about 500 ng/g, less than about 250 ng/g, less than about 100 ng/g, less than about 90 ng/g, less than about 80 ng/g, less than about 70 ng/g, less than about 60 ng/g, or less than about 50 ng/g. In some embodiments, this NNN content represents a reduction of greater than about 25% or greater than about 50% reduction in NNN as compared with the NNN content of a cured tobacco material that has not been treated with a chloride source.

In some embodiments, the NAT content of cured tobacco material that has been treated with a chloride source prior to harvest, as provided herein, can be less than about 500 ng/g, less than about 250 ng/g, less than about 100 ng/g, less than about 90 ng/g, less than about 80 ng/g, less than about 70 ng/g, less than about 60 ng/g, or less than about 50 ng/g. In some embodiments, this NAT content represents a reduction of greater than about 25% or greater than about 50% reduction in NAT as compared with the NAT content of a cured tobacco material that has not been treated with a chloride source. In some embodiments, such values are obtained with respect to a tobacco material that has been treated in an identical manner to the treated tobacco material disclosed herein, with the exception that no chloride source is applied to the plant or soil during/before growth of the plant. For example, in certain embodiments, such values are obtained where KCl is used as the chloride source and are provided in comparison to values obtained where an equivalent amount of another K source (e.g., potassium sulfate) is used in place of the KCl. The whole tobacco plant, or certain parts or portions of the plant of the *Nicotiana* species can be used and/or treated as provided herein. For example, virtually all of the plant (e.g., the whole plant) can be harvested and employed as such. Alternatively, various parts or pieces of the plant can be harvested or separated for treatment after harvest. For example, the flower, leaves, stem, stalk, roots, seeds, and various combinations thereof, can be isolated for use or further treatment.

After treatment, the treated tobacco material can be used in a green form (e.g., the plant or portion thereof can be used without being subjected to any curing process). For example, the plant or portion thereof can be used without being subjected to significant storage, handling or processing conditions. In certain situations, it is advantageous for the plant or portion thereof be used virtually immediately after harvest. Alternatively, for example, a plant or portion thereof in green form can be refrigerated or frozen for later use, freeze dried, subjected to irradiation, yellowed, dried, cured (e.g., using air drying techniques or techniques that employ application of heat), heated or cooked (e.g., roasted, fried or boiled), or otherwise subjected to storage or treatment for later use. It is understood that the benefits, e.g., reduced TSNA formation, enhanced fermentation, and the like, are realized after curing; therefore, the treated materials described herein are advantageously cured prior to use, e.g., in a tobacco product.

The tobacco material can be physically processed (before or after treatment and before or after curing). The plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The tobacco material can have the form of processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina). The tobacco that is used for the tobacco product most preferably includes tobacco lamina, or a tobacco lamina and stem mixture. Portions of the tobaccos within the tobacco product may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the tobacco product optionally may incorporate tobacco that has been fermented. See, also, the types of tobacco processing techniques set forth in PCT WO 05/063060 to Atchley et al., which is incorporated herein by reference.

The manner by which the tobacco is provided in such forms can vary. The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25 weight percent, often less than about 20 weight percent, and frequently less than about 15 weight percent.

Tobacco parts or pieces can be comminuted, ground or pulverized into a powder type of form using equipment and techniques for grinding, milling, or the like. Most preferably, the tobacco is relatively dry in form during grinding or milling, using equipment such as hammer mills, cutter heads, air control mills, or the like. For example, tobacco parts or pieces may be ground or milled when the moisture content thereof is less than about 15 weight percent to less than about 5 weight percent.

Tobacco compositions intended to be used in a smokable or smokeless form may incorporate a single type of tobacco (e.g., in a so-called "straight grade" form). For example, the tobacco within a tobacco composition may be composed solely of flue-cured tobacco (e.g., all of the tobacco may be composed, or derived from, either flue-cured tobacco lamina or a mixture of flue-cured tobacco lamina and flue-cured tobacco stem. The tobacco within a tobacco composition also may have a so-called "blended" form. For example, the tobacco within a tobacco composition of the present invention may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other exemplary tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other exemplary tobacco blends incorporate about 20 to about 30 parts Oriental tobacco and about 70 to about 80 parts flue-cured tobacco.

Tobacco that has been treated according to the present disclosure can, in certain embodiments, be subsequently extracted. Various extraction techniques can be used. See, for example, the extraction processes described in US Pat. Appl. Pub. No. 2011/0247640 to Beeson et al., which is incorporated herein by reference. Other exemplary techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein.

The tobacco materials discussed in the present invention can further be treated and/or processed in other ways before, after, or during the enzymatic treatment described herein. For example, if desired, the tobacco materials can be irradiated, pasteurized, or otherwise subjected to controlled heat treatment. Such treatment processes are detailed, for example, in US Pat. Pub. No. 2009/0025738 to Mua et al., which is incorporated herein by reference. It is noted that, advantageously, in embodiments wherein the treatment solution comprises an enzyme, the enzyme is at least about 75%, at least about 80%, at least about 85%, at least about 90%, at least about 95%, at least about 98%, at least about 99%, or completely deactivated and/or degraded at elevated temperatures. Therefore, in certain embodiment, where the enzyme-treated tobacco is heat-treated and/or used at an elevated temperature (e.g., incorporated within a cigarette, which burns at an elevated temperature), little to no active enzyme may remain in the tobacco material.

In certain embodiments, treated tobacco materials as described herein can be further contacted with water and an additive capable of inhibiting reaction of asparagine to form acrylamide upon heating of the tobacco material (e.g., an additive selected from the group consisting of lysine, glycine, histidine, alanine, methionine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof), and combinations thereof. See, for example, the types of treatment processes described in US Pat. Pub. Nos. 2010/0300463; 2011/0048434; and 2012/0060854, all to Chen et al., which are all incorporated herein by reference. In certain embodiments, this type of treatment is useful where the original tobacco material is subjected to heat in the extraction and/or distillation process previously described.

The treated tobacco can be incorporated within various types of tobacco products according to the present invention. For example, in some embodiments, the invention provides smoking articles, such as cigarettes, that comprise a treated tobacco material that has been subjected to one or more of the types of treatment described herein. Referring to FIG. 1, there is shown a smoking article 10 in the form of a cigarette and possessing certain representative components of a smoking article of the present invention. The cigarette 10 includes a generally cylindrical rod 12 of a charge or roll of smokable filler material (e.g., about 0.3 to about 1.0 g of smokable filler material such as tobacco material treated as described herein) contained in a circumscribing wrapping material 16. The rod 12 is conventionally referred to as a "tobacco rod." The ends of the tobacco rod 12 are open to expose the smokable filler material. The cigarette 10 is shown as having one optional band 22 (e.g., a printed coating including a film-forming agent, such as starch, ethylcellulose, or sodium alginate) applied to the wrapping material 16, and that band circumscribes the cigarette rod in a direction transverse to the longitudinal axis of the cigarette. That is, the band 22 provides a cross-directional region relative to the longitudinal axis of the cigarette. The band 22 can be printed on the inner surface of the wrapping material (i.e., facing the smokable filler material), or less preferably, on the outer surface of the wrapping material. Although the cigarette can possess a wrapping material having one optional band, the cigarette also can possess wrapping material having further optional spaced bands numbering two, three, or more.

At one end of the tobacco rod 12 is the lighting end 18, and at the mouth end 20 is positioned a filter element 26. The filter element 26 positioned adjacent one end of the tobacco rod 12 such that the filter element and tobacco rod are axially aligned in an end-to-end relationship, preferably abutting one another. Filter element 26 may have a generally cylindrical shape, and the diameter thereof may be essentially equal to the diameter of the tobacco rod. The ends of the filter element 26 permit the passage of air and smoke therethrough.

A ventilated or air diluted smoking article can be provided with an optional air dilution means, such as a series of perforations 30, each of which extend through the plug wrap 28. The optional perforations 30 can be made by various techniques known to those of ordinary skill in the art, such as laser perforation techniques. Alternatively, so-called off-line air dilution techniques can be used (e.g., through the use of porous paper plug wrap and pre-perforated tipping paper). The filter element 26 is circumscribed along its outer circumference or longitudinal periphery by a layer of outer plug wrap 28. During use, the smoker lights the lighting end 18 of the cigarette 10 using a match or cigarette lighter. As such, the smokable material 12 begins to burn. The mouth end 20 of the cigarette 10 is placed in the lips of the smoker. Thermal decomposition products (e.g., components of tobacco smoke) generated by the burning smokable material 12 are drawn through the cigarette 10, through the filter element 26, and into the mouth of the smoker.

In certain embodiments, according to the invention, a smoking article comprises tobacco that has been treated as described herein (i.e., treated pre-curing with one or more of a salt and/or sugar solution; a probiotic solution; and/or an enzyme solution). The tobacco within the smoking article can, in some embodiments, comprise only such treated tobacco or can contain varying amounts of treated tobacco in combination with other tobacco materials. For example, the treated tobacco can be present in an amount of about 25% or more, about 50% or more, about 75% or more, about 80% or more, about 85% or more, about 90% or more, about 95% or more, or about 100% based on the weight of all tobacco material in the smoking article. Advantageously, in some embodiments, the salt, sugar, enzyme, and/or probiotic used in the treatment of tobacco materials is not transferred in smoke produced from a cigarette made with such tobacco.

Figure 2:
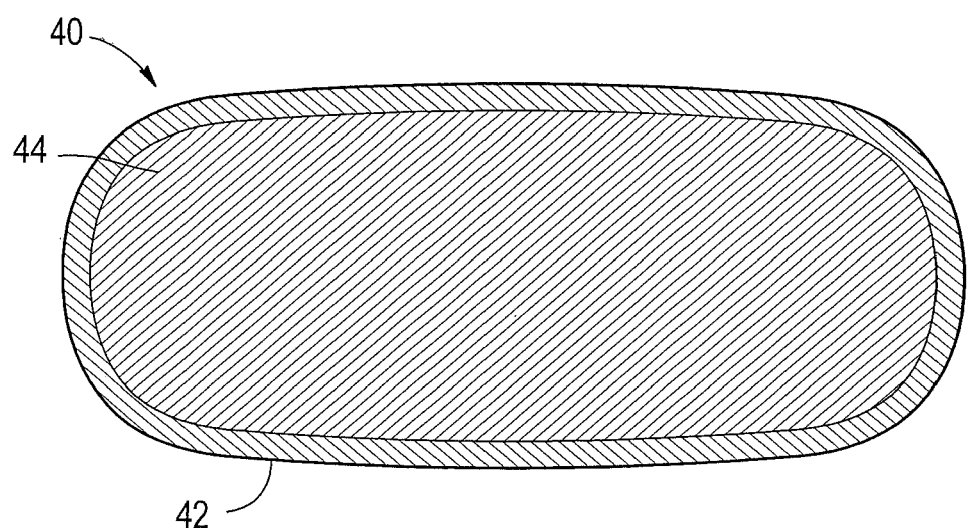
FIG. 2 is a cross-sectional view of a smokeless tobacco product embodiment, taken across the width of the product, showing an outer pouch filled with a smokeless tobacco composition of the invention.

Referring to FIG. 2, a representative snus type of tobacco product comprising treated tobacco as described herein (i.e., tobacco treated with one or more of a salt and/or sugar solution; a probiotic solution; and/or an enzyme solution) is shown. In particular, FIG. 2 illustrates a smokeless tobacco product 40 having a water-permeable outer pouch 42 containing a smokeless tobacco composition 44, wherein the tobacco composition includes a shredded or particulate tobacco material that has been treated as described herein. Further additives can be admixed with, or otherwise incorporated within, the smokeless tobacco compositions according to the invention. The additives can be artificial, or can be obtained or derived from herbal or biological sources. Exemplary types of additives include salts (e.g., sodium chloride, potassium chloride, sodium citrate, potassium citrate, sodium acetate, potassium acetate, and the like), natural sweeteners (e.g., fructose, sucrose, glucose, maltose, vanillin, ethylvanillin glucoside, mannose, galactose, lactose, and the like), artificial sweeteners (e.g., sucralose, saccharin, aspartame, acesulfame K, neotame and the like), organic and inorganic fillers (e.g., grains, processed grains, puffed grains, maltodextrin, dextrose, calcium carbonate, calcium phosphate, corn starch, lactose, manitol, xylitol, sorbitol, finely divided cellulose, and the like), binders (e.g., povidone, sodium carboxymethylcellulose and other modified cellulosic types of binders, sodium alginate, xanthan gum, starch-based binders, gum arabic, lecithin, and the like), pH adjusters or buffering agents (e.g., metal hydroxides, preferably alkali metal hydroxides such as sodium hydroxide and potassium hydroxide, and other alkali metal buffers such as metal carbonates, preferably potassium carbonate or sodium carbonate, or metal bicarbonates such as sodium bicarbonate, and the like), colorants (e.g., dyes and pigments, including caramel coloring and titanium dioxide, and the like), humectants (e.g., glycerin, propylene glycol, and the like), oral care additives (e.g., thyme oil, *eucalyptus* oil, and zinc), preservatives (e.g., potassium sorbate, and the like), syrups (e.g., honey, high fructose corn syrup, and the like), disintegration aids (e.g., microcrystalline cellulose, croscarmellose sodium, crospovidone, sodium starch glycolate, pregelatinized corn starch, and the like), flavorant and flavoring mixtures, antioxidants, and mixtures thereof. If desired, the additive can be microencapsulated as set forth in US Patent Appl. Pub. No. 2008/0029110 to Dube et al., which is incorporated by reference herein. In addition, exemplary encapsulated additives are described, for example, in WO 2010/132444 A2 to Atchley, which has been previously incorporated by reference herein.

EXPERIMENTAL

The present invention is more fully illustrated by the following example, which is set forth to illustrate the present invention and is not to be construed as limiting thereof. Unless otherwise noted, all parts and percentages are by weight, and all weight percentages are expressed on a dry basis, meaning excluding water content, unless otherwise indicated.

Example 1

Dark-air cured tobacco is treated five hours prior to harvest with one or more of a probiotic bacteria solution, and enzyme solution, and/or a 3% sodium chloride salt solution. The solution is applied using a backpack sprayer. Solutions are based on a 100 gallon solution per acre, using recommended plant spacings and dose per plant is provided below.

The treated tobacco is harvested and mid-stalk leaf samples are analyzed for total bacteria counts, enteric bacteria counts, and *Lactobacillus* counts. Ten grams of each treated tobacco sample is placed in Butterfields Phosphate Buffer and diluted $10^{-2}$ to $10^{-8}$ times with water. The treated tobacco sample dilutions are applied to plate count agar (PCA) for total aerobic bacteria counts, to violet red bile agar (VRBA) for gram negative bacteria counts, and to MRS for anaerobic (*Lactobacillus*) counts. The number of bacterial colonies, as visualized under magnification, are counted to estimate the total number of colony-forming units per gram, CFU/g.

Tobacco treated with a probiotic solution available from CVS (solution prepared to provide $6.00 \times 10^9$ CFU per plant) exhibited a total bacteria reduction after treatment of 91%, an enteric bacteria reduction after treatment of 40%, and a *Lactobacillus* reduction after treatment of 46% (all based on total bacteria counts before and after treatment).

Tobacco treated with a probiotic solution available from Walgreens (solution prepared to provide 6.40×10$^9$ CFU per plant) exhibited a total bacteria reduction after treatment of 96%, an enteric bacteria reduction after treatment of 58%, and a *Lactobacillus* reduction after treatment of 42% (all based on total bacteria counts before and after treatment).

Tobacco treated with a probiotic solution available from CVS (solution prepared to provide 6.00×10$^9$ CFU per plant) in combination with a surfactant (Surf-Ac® from Drexel Chemical Company) exhibited a total bacteria reduction after treatment of 95%, an enteric bacteria reduction after treatment of 66%, and a *Lactobacillus* increase after treatment of 57% (all based on total bacteria counts before and after treatment).

Tobacco treated with a *Lactobacillus plantarum* probiotic solution (solution prepared to provide 6.64×10$^{10}$ CFU per plant) exhibited a total bacteria reduction after treatment of 95%, an enteric bacteria reduction after treatment of 75%, and a *Lactobacillus* increase after treatment of 43% (all based on total bacteria counts before and after treatment).

Tobacco treated with a *Lactobacillus acidophilus* probiotic solution (solution prepared to provide 2.72×10$^{10}$ CFU per plant) exhibited a total bacteria reduction after treatment of 93%, an enteric bacteria reduction after treatment of 20%, and a *Lactobacillus* reduction after treatment of 33% (all based on total bacteria counts before and after treatment).

Tobacco treated with a *Bifidobacterium lactis* probiotic solution (solution prepared to provide 4.16×10$^{10}$ CFU per plant) exhibited a total bacteria reduction after treatment of 82%, an enteric bacteria reduction after treatment of 25%, and a *Lactobacillus* reduction after treatment of 16% (all based on total bacteria counts before and after treatment).

Tobacco treated with a *Lactobacillus helveticus* probiotic solution (solution prepared to provide 5.20×10$^9$ CFU per plant) exhibited a total bacteria reduction after treatment of 97%, an enteric bacteria reduction after treatment of 39%, and a *Lactobacillus* increase after treatment of greater than 400% (all based on total bacteria counts before and after treatment).

Tobacco treated with a PreventASe™ enzyme solution (solution prepared to provide 3.2 mL asparaginase per plant) exhibited a total bacteria reduction after treatment of 88%, an enteric bacteria reduction after treatment of 75%, and a *Lactobacillus* reduction after treatment of 43% (all based on total bacteria counts before and after treatment).

Tobacco treated with a 3% NaCl solution exhibited a total bacteria reduction after treatment of 94%, an enteric bacteria reduction after treatment of 76%, and a *Lactobacillus* increase after treatment of greater than 400% (all based on total bacteria counts before and after treatment).

The data of Example 1 illustrates that all treatment solutions provided in a decrease in total bacteria associated with the treated tobacco material (as compared with the tobacco material prior to treatment). The salt (NaCl)-treated tobacco material exhibited a significant increase in desirable *Lactobacillus* bacteria. This finding may render such NaCl (and other salt)-treated tobacco materials particularly suitable for further fermentation processes and for incorporation of such fermented tobacco materials into smokeless tobacco products. Additionally, the *Lactobacillus helveticus*-treated tobacco material exhibited a substantial increase in *Lactobacillus* bacteria after treatment. Although some increase might be expected due to the presence of *Lactobacillus* bacteria in the treatment solution, the increase is much higher than that noted for other *Lactobacillus* probiotic solution-treated tobacco materials (e.g., tobacco treated with *Lactobacillus plantarum* exhibited only a 43% increase and tobacco treated with *Lactobacillus acidophilus* exhibited a 33% decrease in *Lactobacillus* bacteria). Consequently, *Lactobacillus helveticus*-treated tobacco materials may be particularly well suited for further fermentation processes and incorporation of such fermented tobacco materials into smokeless tobacco products as well.

Example 2

A first, 0.5 acre unplanted plot of soil was treated with a nitrogen-containing fertilizer comprising urea (N—P—K: 46-0-0) at a rate of 150 pounds per acre and a fertilizer incorporating diammonium phosphate and phosphorus (N—P—K: 18-46-0) at a rate of 180 pounds per acre by broadcast application. The following day, a potassium sulfate fertilizer (N—P—K: 0-0-50) was broadcast applied at 180 pounds per acre. All fertilizer applications were incorporated into the soil after application.

A second, 0.5 acre unplanted plot of soil was treated with a nitrogen-containing fertilizer comprising urea (N—P—K: 46-0-0) at a rate of 150 pounds per acre and a fertilizer incorporating diammonium phosphate and phosphorus (N—P—K: 18-46-0) at a rate of 180 pounds per acre by broadcast application. The following day, a potassium chloride fertilizer (N—P—K: 0-0-60) was broadcast applied at 180 pounds per acre. All fertilizer applications were incorporated into the soil after application.

Dark tobacco plants were independently grown and were transplanted as seedlings (approximately 6-10 inches in length) to both plots (with 2450 plants per fertilized plot) four days after application of the potassium sources to the soil. Approximately four weeks after transplanting, both plots were side dressed with urea-ammonium nitrate (UAN-32% liquid N). The tobacco plants from both plots were harvested about three months after UAN treatment, and the harvested plants were moved to a traditional 1-acre air-curing barn. The plants were cured in the barn for about a month and a half.

After curing the plants, the leaves were removed from the stalks. The fourth leaf from the upper stalk position of six plants from each plot was taken for analysis. Each of these twelve leaves was prepared by removing the mid-rib stem from the leaf lamina.

The lamina was milled and the content of certain components was evaluated by liquid chromatography-mass spectrometry (LCMS). In particular, the leaves were analyzed in triplicate for TSNA content (namely, NNN, NNK, NAT, and NAB content). Test results demonstrated that TSNA levels, and particularly NNN and NNK levels are significantly lower for the leaves derived from potassium chloride-treated soil as compared with the leaves derived from potassium sulfate-treated soil. Data on this analysis is provided below in Table 1.

TABLE 1

Comparison of TSNA levels in cured tobacco leaves grown in soil treated with potassium chloride and potassium sulfate

| Potassium Chloride Treatment (Plot 2) | Moisture | NNN ng/g | NAT ng/g | NAB <ng/g | NNK ng/g |
|---|---|---|---|---|---|
| Sample 1 | 17.7 | <41.2 | 46.5 | <10.2 | <40.8 |
| Sample 2 | 16.1 | 41.4 | 53.9 | <10.1 | <40.5 |
| Sample 3 | 16.7 | <41.9 | <41.9 | <10.4 | <41.4 |
| Sample 4 | 17.1 | 43.2 | 66.7 | <10.3 | <40.9 |

TABLE 1-continued

Comparison of TSNA levels in cured tobacco leaves grown in soil treated with potassium chloride and potassium sulfate

| Sample 5 | 17.8 | <40.6 | <40.6 | <10.1 | <40.2 |
| Sample 6 | 15.6 | <41.2 | <41.2 | <10.2 | <40.8 |

| Potassium Sulfate Treatment (Plot 1) | Moisture | NNN ng/g | NAT ng/g | NAB ng/g | NNK ng/g |
| --- | --- | --- | --- | --- | --- |
| Sample 1 | 15.3 | 174 | 288 | <10.21 | <39.7 |
| Sample 2 | 16.3 | 172 | 216 | <10.1 | <40.1 |
| Sample 3 | 17.70 | 153 | 325 | <10.2 | <40.9 |
| Sample 4 | 12.2 | 161 | 229 | <10 | <39.9 |
| Sample 5 | 18.54 | 80.2 | 127 | <10.3 | <41.4 |
| Sample 6 | 16.20 | 76.2 | 100 | 10 | <40.1 |

As demonstrated by the data in Table 1, treatment of soil with potassium chloride prior to transplanting tobacco plants therein, as compared with treatment with potassium sulfate, led to significant decreases in NNN and NAT content in all cured leaf samples tested. In fact, in potassium chloride-treated samples 1, 2, 3, 5, and 6, NNN content was below the level of quantification. In potassium chloride-treated samples 3, 5, and 6, NAT content was below the level of quantification. As shown, NNN and NAT content in all potassium sulfate-treated samples was well above such levels. The potassium-chloride treated samples exhibited an average decrease of about 69% NNN with respect to the potassium sulfate-treated samples and an average decrease of about 77% NAT with respect to the potassium sulfate-treated samples.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A method of reducing TSNA content of a tobacco material, comprising:
   growing a tobacco plant in soil treated with a chloride source;
   harvesting the tobacco plant; and
   curing the harvested tobacco plant to give a cured tobacco material,
   wherein said method provides a treated, cured tobacco material having a TSNA content that is reduced as compared to a cured tobacco material that has been grown in soil not treated with a chloride source, wherein the soil is treated with the chloride source in an amount of about 25 to about 150 lbs per acre.

2. The method of claim 1, further comprising planting tobacco prior to the soil treatment.

3. The method of claim 1, further comprising planting tobacco after the soil treatment.

4. The method of claim 1, further comprising applying the chloride source to the soil.

5. The method of claim 4, wherein the chloride source is a chloride salt.

6. The method of claim 4, wherein the chloride source is a compound capable of decomposition to provide chloride ions.

7. The method of claim 4, wherein the chloride source is selected from the group consisting of sodium chloride (NaCl), potassium chloride (KCl), magnesium chloride ($MgCl_2$), calcium chloride ($CaCl_2$), and combinations thereof.

8. The method of claim 4, wherein the chloride source is KCl.

9. The method of claim 1, wherein the chloride source comprises one or more fertilizer components, selected from the group consisting of nitrogen, potassium, and phosphorus.

10. The method of claim 4, wherein the applying comprises applying the chloride source in solid form to the soil.

11. The method of claim 4, wherein the applying comprises applying a solution of the chloride source to the soil.

12. The method of claim 1, wherein the combined content of NNN, NAT, NAB, and NAK in the treated, cured tobacco material is less than about 500 ng/g.

13. The method of claim 1, wherein the combined content of NNN, NAT, NAB, and NAK in the treated, cured tobacco material is less than about 200 ng/g.

14. The method of claim 1, wherein the NNN content in the treated, cured tobacco material is less than about 100 ng/g.

15. The method of claim 1, wherein the NNN content in the treated, cured tobacco material is less than about 50 ng/g.

16. The method of claim 1, wherein the NAT content in the treated, cured tobacco material is less than about 100 ng/g.

17. The method of claim 1, wherein the NAT content in the treated, cured tobacco material is less than about 75 ng/g.

18. The method of claim 1, wherein the combined NAT and NNN content in the treated, cured tobacco material is less than about 150 ng/g.

19. The method of claim 1, wherein the NNN content in the treated, cured tobacco material represents greater than a 50% reduction as compared with that of a cured tobacco material from a plant grown in soil with comparable levels of N, P, and K but without any chloride source added thereto.

20. The method of claim 1, wherein the NAT content in the treated, cured tobacco material represents greater than a 50% reduction as compared with that of a cured tobacco material from a plant grown in soil with comparable levels of N, P, and K but without any chloride source added thereto.

21. The method of claim 1, wherein the curing comprises air curing.

22. The method of claim 1, wherein the curing comprises fire curing.

23. The method of claim 1, further comprising:
   processing the treated, cured tobacco material to provide a processed tobacco material in a form suitable for incorporation in a tobacco product; and
   incorporating the processed tobacco material into a smokeless tobacco product.

24. The method of claim 23, wherein the processed tobacco material is in the form of cut filler.

25. The method of claim 23, wherein the processed tobacco material is in the form of a tobacco blend.

* * * * *